United States Patent
Hall et al.

(10) Patent No.: US 6,508,768 B1
(45) Date of Patent: Jan. 21, 2003

(54) ULTRASONIC ELASTICITY IMAGING

(75) Inventors: Timothy J. Hall, Shawnee, KS (US); Yanning Zhu, Lenexa, KS (US)

(73) Assignee: University of Kansas Medical Center, Kansas City, KS (US)

( * ) Notice: Subject to any disclaimer, the term of this patent is extended or adjusted under 35 U.S.C. 154(b) by 18 days.

(21) Appl. No.: 09/955,661

(22) Filed: Sep. 17, 2001

Related U.S. Application Data
(60) Provisional application No. 60/253,031, filed on Nov. 22, 2000.

(51) Int. Cl.$^7$ .................................................. A61B 8/00
(52) U.S. Cl. .................................................... 600/443
(58) Field of Search ............................... 600/437, 440, 600/443, 447, 449, 589; 73/602, 573, 787

(56) References Cited

U.S. PATENT DOCUMENTS

| | | | |
|---|---|---|---|
| 5,107,837 A | | 4/1992 | Ophir et al. ............ 128/660.01 |
| 5,143,070 A | | 9/1992 | Ophir et al. ............ 128/660.01 |
| 5,178,147 A | | 1/1993 | Ophir et al. ............ 128/660.01 |
| 5,249,238 A | * | 9/1993 | Komerath et al. .............. 382/1 |
| 5,293,870 A | | 3/1994 | Ophir et al. ............ 128/660.01 |
| 5,474,070 A | | 12/1995 | Ophir et al. ............ 128/660.01 |
| 5,495,771 A | * | 3/1996 | Sumi et al. ..................... 73/789 |
| 5,503,153 A | * | 4/1996 | Liu et al. .................. 73/861.25 |
| 5,524,636 A | * | 6/1996 | Sarvazyan et al. ........... 600/589 |
| 5,538,004 A | * | 7/1996 | Bamber ....................... 128/916 |
| 5,579,771 A | * | 12/1996 | Bonnefous ................... 600/440 |
| 5,839,441 A | * | 11/1998 | Steinberg ..................... 128/898 |
| 5,873,830 A | * | 2/1999 | Hossack et al. ............. 600/447 |
| 5,959,139 A | * | 9/1999 | Lin .............................. 600/443 |
| 6,068,597 A | * | 5/2000 | Lin .............................. 600/443 |
| 6,095,976 A | * | 8/2000 | Nachtomy et al. ........... 600/443 |
| 6,099,471 A | * | 8/2000 | Torp et al. ................... 600/438 |
| 6,176,827 B1 | * | 1/2001 | Cohen-Bacrie et al. ...... 600/438 |
| 6,270,459 B1 | * | 8/2001 | Konofagou et al. ......... 600/449 |
| 6,352,507 B1 | * | 3/2002 | Torp et al. ................... 600/438 |
| 6,368,277 B1 | * | 4/2002 | Mao et al. ................... 600/441 |
| 6,371,912 B1 | * | 4/2002 | Nightingale et al. ........ 600/437 |
| 2002/0040187 A1 | * | 4/2002 | Alam et al. .................. 600/442 |

FOREIGN PATENT DOCUMENTS
| | | | |
|---|---|---|---|
| WO | WO 99/61903 | 12/1999 | .......... G01N/29/00 |

OTHER PUBLICATIONS
S.K. Alam, J. Ophir, and E.E. Konofagou, "An adaptive strain estimator for elastography," IEEE Trans. Ultrason. Ferroelect. Freq. Contr. 45(2):461–472, 1998.

S.K. Alam, and J. Ophir, "Reduction of signal decorrelation from mechanical compression of tissues by temporal stretching: Application to elastography," Ultrason. Med. Biol. 23(1):95–105, 1997.

(List continued on next page.)

*Primary Examiner*—Francis J. Jaworski
(74) *Attorney, Agent, or Firm*—Jeffrey Slusher

(57) ABSTRACT

In an ultrasound imaging system, a displacement vector is estimated for a pattern of samples throughout an imaged region of interest (ROI) by comparing two successive B-mode frames. The displacement vector is preferably estimated using block matching. Once displacement vectors are estimated for samples throughout the ROI, corresponding strain values are estimated, which indicate the degree of elasticity of the respective tissue portions. An image is then displayed showing the strain distribution within the ROI as it is stressed, for example, by the user pressing the ultrasound transducer against the patient's body. The invention allows for both real-time and post-processed generation of elasticity displays, even based on the same body of acquired frame data. The real-time display is preferably generated using lower quality block matching whereas the post-processed elasticity calculations are carried out using high-quality techniques. Different techniques are included for adjusting the size and location of the search region of the block matching based on different measures of reliability of current displacement estimates.

28 Claims, 4 Drawing Sheets

OTHER PUBLICATIONS

M. Bertrand, J. Meunier, M. Doucet, and G. Ferland, "Ultrasonic biomechanical strain gauge based on speckle tracking," IEEE Ultrasonics Symposium Proc 89CH2791–2:859–863, 1989.

M. Bierling, "Displacement estimation by hierarchical block–matching," Proc. Visual Comm. and Image Proc, SPIE 1001:942–951, 1988.

M. Bilgen and M.F. Insana, "Deformation models and correlation analysis in elastography," J Acoust. Soc. Am 99(5): 3212–3224, 1996.

M. Bilgen and M.F. Insana, "Error analysis in acoustic elastography: I. displacement estimation,"J Acoust. Soc. Am. 101(2):1139–1146, 1997.

M. Bilgen and M.F. Insana, "Error analysis in acoustic elastography: II. strain estimation and SNR analysis," J. Acoust. Soc. Am. 101(2):1147–1154, 1997.

E.I. Cespedes, C.L. de Korte, A.F.W. van der Steen, "Echo decorrelation from displacement gradients in elasticity and velocity estimation," IEEE Trans Ultrason, Ferroelec, Freq Control 46(4):791–801, 1999.

E.I. Cespedees, M.F. Insana, and J. Ophir, "Theoretical bounds on strain estimation in elastography," IEEE Trans Ultrason Ferro Freq Contr 42(5):969–972, 1995.

E.I. Cespedes and J. Ophir, "Reduction of image noise in elastography," Ultrasonic Imaging 15:89–102, 1993.

E.I. Cespedes, J. Ophir, H. Ponnekanti, and N. Maklad, "Elastography: Elasticity imaging using ultrasound with application to muscle and breast in vivo," Ultrason Imaging 15:73–88, 1993.

P. Chaturvedi, M.F. Insana, and T.J. Hall, "2–D companding for noise reduction in strain imaging," IEEE Trans Ultrason Ferroelect Freq Contr 45(1):179–191, 1998.

P. Chaturvedi, M.F. Insana, and T.J. Hall, "Testing the limitations of 2–D local companding in strain imaging using phantoms," IEEE Trans. Ultrason Ferroelect Freq Contr 45(4):1022–1031, 1998.

R. Cusani, "Fast techniques for time delay estimation," Proc. MELECON '89 177–180, 1989.

P.G.M. De Jong, T. Arts, and A.P.G. Hoeks, "Determination of tissue motion velocity by correlation interpolation of pulsed ultrasound echo signals," Ultrasonic Imaging 12:84–98, 1990.

R. J. Dickinson and C.R. Hill, "Measurement of soft tissue motion using correlation between A scans," Ultrasound Med Biol 8(3):263–271, 1982.

D. Dotti, E. Gatti, V. Svelto, A. Ugge, and P. Vidali, "Blood flow measurements by ultrasound correlation techniques," Energia Nucleare 23:571–575, 1976.

M..M. Doyley, J.C. Bamber, F. Fuechsel, N.L. Bush, "A freehand elastographic approach for clinical breast imaging: System development and performance evaluation," Ultrasound in Medicine and Biology 27(10):1347–1357, 2001.

S.Y. Emelianov, M.A. Lubinski, A.R. Skovoroda, et al., "Reconstructive ultrasound elasticity imaging for renal transplant diagnosis: Kidney ex vivo results," Ultrasonic Imaging 22:178–194, 2000.

L. Gao, K.J. Parker, R.M. Lerner, and S.F. Levinson, "Imaging of the elastic properties of the tissue: A review," Ultrason Med Biol 22(8):959–977, 1996.

B.S. Garra, E.I. Cespedes, J. Ophir, S.R. Spratt, R.A. Zuurbier, C.M. Magnant, and M.F. Pennanen, "Elastography of breast lesions: initial clinical results, " Radiology 202(1):79–86, 1997.

H. Gharavi and M. Mills, "Block–matching motion estimation algorithms: new results," IEEE Trans Circ and Syst 37:649–651, 1990.

M.F. Insana, P. Chaturvedi, T.J. Hall, and M. Bilgen, "3–D companding using linear arrays for improved strain imaging," IEEE Ultrasonics Symposium Proc 97CH36118:1435–1438, 1997.

M.F. Insana, L.T. Cook, M. Bilgen, P. Chaturvedi, and Y. Zhu, "Maximum–likelihood approach to strain imaging using ultrasound," J Acoust. Soc. Am. 107(3):1421–1434, 2000.

J.R. Jain and A.K. Jain, "Displacement measurement and its application in interframe image coding," IEEE Trans. Commun. 29:1799–1808, 1981.

C.H. Knapp and G.C. Carter, "The generalized correlation method for estimation of time delay," IEEE Trans Acoust, Speech, Signal Processing 24(4):320–327, 1976.

T.A. Krouskop, D.R. Dougherty, and S.F. Vinson, "A pulsed Doppler ultrasonic system for making non–invasive measurements of the mechanical properties of soft tissues," J Rehab Res Dev 24(2):1–8, 1987.

W. Leucht, D.R. Rabe, and K–D Humbert, "Diagnostic Value of Different Interpretive Criteria in Real–Time Sonography of the Breast," Ultrason Med Biol 14(1):59–73, 1988.

Lorenz, H–J. Sommerfeld, M. Garcia–Schurmann, et al., "A new system for the acquisition of ultrasonic multicompression strain images of the human prostate in vivo," IEEE Trans Ultrason, Ferroelec, Freq Control 46(5):1147–1154, 1999.

A. Lubinski, S.Y. Emelianov, M. O'Donnell, "Adaptive strain estimator using retrospective processing," IEEE Trans Ultrason, Ferroelec, Freq Control 46(1):97–1107, 1999.

M. O'Donnell, A.R. Skovoroda, and B.M. Shape, "Measurement of arterial wall motion using Fourier based speckle tracking algorithms," IEEE Ultrasonic Symposium Proc. 1101–1104, 1991.

M. O'Donnell, A.R. Skovoroda, B.M. Shapo, and S. Emelianov, "Internal displacement and strain imaging using ultrasonic speckle tracking," IEEE Trans Ultrason, Ferro, Freq Contr 41(3):314–325, 1994.

J. Ophir, E.I. Cespedes, H. Ponnekanti, Y. Yazdi, and X. Li, "Elastography: a quantitative method for imaging the elasticity of biological tissues," Ultrasonic Imaging 13:111–134, 1991.

G.E. Trahey, S.M. Hubbard, and O.T. Von Ramm, "Angle independnet blood flow detection by frame–to–frame correlation of B–mode images," Ultrasonics 26:271–276, 1988.

M. Tristam, D. C. Barbosa, D. O. Cosgrove, D. K. Nassiri, J. C. Bamber, and C. R. Hill, "Ultrasonic study of in vivo kinetic characteristics of human tissues," Ultrason Med Biol 12(12):927–937, 1986.

M. Tristam, D. C. Barbosa, D. O. Cosgrove, J. C. Bamber, and C. R. Hill, "Application of Fourier Analysis to Clinical Study of Patterns of Tissue Movementt,"Ultrason Med Biol 14(8):695–707, 1988.

E. Ueno, et al., "Dynamic Tests in Real–Time Breast Elastography," Ultrason Med Biol 14(1):53–57, 1988.

T. Varghese, J. Ophir, and E.I. Cespedes, "Noise reduction in elastograms using temporal stretching with multicompression averaging," Ultrasound in Med Biol 22(8):1043–1052, 1996.

L.S. Wilson and D.E. Robinson, "Ultrasonic measurement of small displacements and deformations of tissues," Ultrasonic Imaging 4:71–82, 1982.

F. Yeung, S.F. Levinson, D. Fu, and K.J. Parker, "Feature-adaptive motion tracking of ultrasound image sequences using a deformable mesh," IEEE Trans Medical Imaging 17(6):945–956, 1998.

F. Yeung, S.F. Levinson, and K.J. Parker, "Multilevel and motion model–based ultrasonic speckel tracking algorithms," Ultrasound in Med and Biol 24(3):427–441, 1998.

Y. Zhu, P. Chaturvedi, and M.F. Insana, "Strain imaging with a deformable mesh," Ultrasonic Imaging 21:127–146, 1999.

Y. Zhu, M.F. Insana, P. Chaturvedi, T.J. Hall, H. Khant, L.T. Cook, and J.M. Gauch, Deformable mesh algorithm for strain imaging with complex tissue deformation, IEEE Ultrasonics Symposium Proc 98CH36102:1769–1772, 1998.

* cited by examiner

ULTRASONIC ELASTICITY IMAGING

CROSS-REFERENCE TO RELATED APPLICATIONS

This application claims priority of pending U.S. Provisional Patent Application No. 60/253,031, filed Nov. 22, 2000.

STATEMENT REGARDING GOVERNMENT RIGHTS

This invention was made with Government support under grant number BES-9708221 awarded by the National Science Foundation. The Government has certain rights in this invention.

BACKGROUND OF THE INVENTION

1. Technical Field

This invention relates to diagnostic ultrasonic imaging in general and to ultrasonic imaging of the elastic properties of scanned tissue in particular.

2. Description of the Related Art

Tissue elastic properties convey important diagnostic information. Consequently, palpation—the pressing of tissue to feel for differences in elasticity—has been used since ancient times as a simple but effective diagnostic technique. Even to this day, for example, most breast cancers are discovered by self-examination using manual palpation, and physicians still rely on palpation to detect potential tumors of the liver and prostate.

The principle of manual palpation is accordingly well known and is based on the property that if a compressive force is applied to an elastic body, then it will deform. If a relatively stiffer, that is, less deformable, inclusion is located within a region of the body, then a constant compressive displacement will deform the region above the stiff object more than the adjacent regions. Because tissues are elastic, the more they are deformed, the greater counter force they generate; in other words, large stress leads to large deformation. If a diagnostician applies the pressure with her fingers, then she will often be able to feel the stress distribution above the palpated region. To sum up the procedure, if one presses on body tissue, then one can often feel "lumps."

One property of tissue elasticity that is not as intuitive is that the distribution of stress that results from a compressive force applied to the top of the region under investigation is not uniform throughout the region. Rather, the stress difference that is large close to the target decays rapidly further from the target. In other words, differences in tissue stiffness are not as noticeable when the stiffer object is deeper within the body. Stress decay therefore limits the depth at which one can palpate tumors manually—if the tumor is too deep, then one cannot feel it at all.

Ultrasonic elasticity imaging is a technique that emulates palpation. According to this technique, an ultrasound transducer is used as a remote sensing device to scan an object within an interrogation region of the body both before and after a compression is applied. The 2-D displacement function is then estimated by comparing the pre- and post-compression scans. Object strain and/or elastic constants can then be estimated from the estimated displacement function.

Ultrasonic elasticity imaging has several advantages over palpation. One advantage is that it can provide information about tissue elasticity as deep as the ultrasound can penetrate, whereas manual palpation senses stress only near the surface. Another advantage is that ultrasonic elasticity imaging has relatively high sensitivity, although resolution and sensitivity can be reduced for deeper inclusions. Ultrasonic elasticity imaging can also provide a 2-D cross sectional view of the elastic properties of the object that are within the sound beam. For example, using axial strain images, one can often detect malignant lesions and estimate their location and geometry. One other obvious advantage of ultrasonic elasticity imaging is that the image acquisition process is non-invasive and poses no risk to patients.

With these advantages, ultrasonic elasticity imaging has found many applications such as tumor detection, assessment of early renal disease, and vascular disease diagnosis. Moreover, because the elastic properties of tissue play an important role in tissue characterization, many more clinical applications can be found once image quality can be reliably maintained. Examples of known applications of ultrasonic elasticity imaging are disclosed in:

M. Bilgen and M. F. Insana, "Deformation models and correlation analysis in 9 elastography," J. Acoust. Soc. Am. 99(5): 3212–3224, 1996;

I. Cespedes, J. Ophir, H. Ponnekanti, and N. Maklad, "Elastography: Elasticity imaging using ultrasound with application to muscle and breast in vivo," Ultrason. Imaging 15: 73–88, 1993;

E. J. Chen, R. S. Adler, P. L. Carson, W. K. Jenkins, and W. D. O'Brien, "Ultrasound tissue displacement imaging with application to breast cancer," Ultrason. Med. Biol. 21(9): 1153–1162, 1995;

B. S. Garra, E. I. Cespedes, J. Ophir, S. R. Spratt, R. A. Zuurbier, C. M. Magnant, and M. F. Pennanen, "Elastography of breast lesions: initial clinical results," Radiology 202(1):, 79–86, 1997;

T. J. Hall, P. Chaturvedi, M. F. Insana, J. G. Wood, H. Khant, and Y. Zhu, "Tracking progressive renal disease with quantitative ultrasonic imaging," IEEE "Ultrasonics Symposium Proc. 98CH36102: 1769–1772, 1998;

S. H. Huang, "Principles of sonoelasticity imaging and its applications in hard tumor detection," Ph.D. thesis, University of Rochester, Rochester, N.Y., 1990;

T. A. Krouskop, D. R. Dougherty, and S. F. Vinson, "A pulsed Doppler ultrasonic system for making non-invasive measurements of the mechanical properties of soft tissues," J. Rehab Res Dev 24(2):1–8, 1987;

M. Krueger, A. Pesavento, H. Ermert, K. M. Hiltawsky, L. Heuser, H. Rosenthal, and A. Jensen, "Ultrasonic strain imaging of the female breast using phase root seeking and three-dimensional 'optical flow'," IEEE Ultrasonics Symposium Proc. 98CH36102: 1757–1760, 1998;

L. Gao, K. J. Parker, R. M. Lerner, and S. F. Levinson, "Imaging of the elastic properties of the tissue: A review," Ultrason. Med. Biol. 22(8): 959–977, 1996;

K. Motoi, H. Morita, N. Fujita, Y. Takano, K. Muzushige, S. Senda, and S H. Matsuo, "Stiffness of human arterial wall assessed by intravascular ultrasound," J. Cardio. 25: 189–197, 1995;

J. Ophir, E. I. Cespedes, H. Ponnekanti, Y. Yazdi, and x. Li, "Elastography: a quantitative method for imaging the elasticity of biological tissues," Ultrasonic Imaging 13: 111–134, 1991;

A. P. Sarvazyan, A. R. Skovoroda, S. Y. Emelianov, J. B. Fowikes, J. G. Pipe, R. S. Adler, R. B. Buxton, and P. L. Carson, "Biophysical bases of elasticity imaging," Acoust. Imaging 21:223–240, 995; and M. Tristam, D. C. Barbosa, D. O. Cosgrove, D. K. Nassiri, J. C. Bamber, and C. R. Hill, "Ultrasonic study of in vivo kinetic characteristics of human tissues," Ultrason. Med. Biol. 12(12): 927–937, 1986.

There are, accordingly, several displacement/strain estimation methods in the prior art. The algorithms underlying these known methods typically rely on cross-correlation, echo data modeling, block matching, direct strain estimation using adaptive local stretching algorithm, and the analysis of a deformable model. These known methods are outlined here.

Cross-correlation techniques have been widely used in sonar and radar systems since their inception in the 1940's. In sonar, marine vessels tow an array of acoustic sensors. A passive, 1-D sonar array then listens for externally generated sound while an active sonar system transmits sound pulses and listens for corresponding echoes. The time delays between signals received by different sensors in the array are then computed using cross-correlation. The relative distance and bearing of the echo source can then be computed from the estimated time delay.

Cross-correlation has also been applied to the problem of estimating the elastic properties of biological tissue. Published International Patent Application PCT/EP99/03769, "System for Rapidly Calculating Expansion Images from High-Frequency Ultrasonic Echo Signals," Pesa Vento and Helmut Ermert, published Dec. 2, 1999. The displacement in time between at least two different echo signals is determined by iteratively evaluating the phases of a plurality of the complex values of the cross-correlation function. In order to achieve the desired speed, this method restricts evaluation to echo signals from points on the same A-line.

The general time delay estimation problem can be stated more rigorously as follows: A signal, s(t), which is generated by a remote source, is detected by two sensors. Because the distances between the sensors and the source are different, the detected signals from these sensors can be written as:

$$s_1(t)=s(t)+n_1(t)$$
$$s_2(t)=s(t+D)+n_2(t)$$

where D is the time delay; and $n_1(t)$ and $n_2(t)$ are noise processes that are independent of s(t). In this data model, one assumes that s(t) is a deterministic signal, that the speed of sound c is constant, and that the delay D is independent of time. The time delay estimation problem thus involves estimating D from the observed signals $s_1(t)$ and $s_2(t)$. The details of different time-delay estimation methods can be found in:

E. K. Al-Hussaini and S. A. Kassam, "Robust Eckart filters for time delay estimation," IEEE Trans. Acoust., Speech, Signal Processing 32(5): 1052–1063, 1984;

R. Cusani, "Fast techniques for time delay estimation," Proc. MELECON '89 177–180, 1989; and C. H. Knapp and G. C. Carter, "The generalized correlation method for estimation of time delay," IEEE Trans. Acoust., Speech, Signal Processing 24(4): 320–327, 1976.

The performance of time-delay estimation techniques is analyzed in, for example:

E. Weinstein and A. Weiss, "Fundamental limitations in passive time delay estimation-part I: narrow-band systems," IEEE Trans. Acoust., Speech, Signal Processing 31(2): 472–485, 1983; and "Fundamental limitations in passive time delay estimation-part II: wide-band systems," IEEE Trans. Acoust., Speech, Signal Processing 32(5): 1064–1077, 1984.

Medical ultrasonic elasticity imaging is analogous to time-delay estimation as described above, although s(t) is usually stochastic and D is often a function of time. When it is appropriate to assume a constant sound speed, time delay will still be directly proportional to displacement. On the other hand, stochastic signals and time-dependent delays greatly increase the complexity of displacement estimation in medical ultrasonic elasticity imaging as compared with the simpler time-delay problem found in sonar.

The echo data model for a deformed biological medium can be summarized as follows: Assume that tissue-scattering sources located within the interrogation region of the body may be described by a 3-D function z(x), where x is a point in 3-D space. The pre- and post-compression echo signals can then be written as:

$$r_1(x)=[h\hat{*}z](x)+m(x)$$
$$r_2(x)=[h\hat{*}z](x+\Delta(x)+n_2(x))$$

where h is a function that describes the imaging system, $\Delta(x)$ is a function that describes the tissue deformation, and h and z are convolved. The goal is then to estimate the function $\Delta(x)$ from the observed signals $r_1$ and $r_2$.

The complexity of this method for soft-tissue displacement estimation stems from two aspects that can be inferred from the equations. First, if the deformation applied to the tissue is on the order of or larger than the resolution of the imaging system, represented by h, then $r_1$ and $r_2$ will decorrelate and it will be impossible to track object motion. This model for the echo signals is shown in, for example, R. F. Wagner, S. W. Smith, J. M. Sandrik, and H. Lopez, "Statistics of speckle in ultrasound B-scans," IEEE Trans Sonics and Ultrasonics 30(3): 156–163, 1983. In other words, the echo waveforms found in $r_1$ are not always present in $r_2$ so that echo signals are not conserved under deformation. If this happens, then displacement cannot be estimated. Second, unlike in sonar applications, where D is independent of time, the displacement of a deformed tissue in sonography can be an arbitrary function of time. As will become clear from the discussion below, general displacement in medical ultrasonography is a problem in which thousands of variables must be estimated.

In the early works of soft tissue displacement estimation, tissue displacement is approximated by piece-wise constants: Each A-line is divided into equal-length segments and a single delay value is estimated for each segment. Examples of the use of this method are found in:

R. J. Dickinson and C. R. Hill, "Measurement of soft tissue motion using correlation between A scans," Ultrasound Med. Biol. 8(3): 263–271, 1982;

D. Dotti, E. Gatti, V. Svelto, A. Ugge, and P. Vidali, "Blood flow measurements by ultrasound correlation techniques," Energia Nucleare 23: 571–575, 1976;

P. G. M. De Jong, T. Arts, and A. P. G. Hoeks, "Determination of tissue motion velocity by correlation interpolation of pulsed ultrasonic echo signals," Ultrasonic Imaging 12: 84–98, 1990;

M. O'Donnell, A. R. Skovoroda, and B. M. Shapo, "Measurement of arterial wall motion using Fourier based speckle tracking algorithms," IEEE Ultrasonic Symposium Proc. 1101–1104, 1991;

M. O'Donnell, A. R. Skovoroda, B. M. Shapo, and S. Emelianov, "Internal displacement and strain imaging using ultrasonic speckle tracking," IEEE Trans. Ultrason. Ferro Freq. Contr. 41(3): 314–325, 1994;

J. Ophir, E. I. Cespedes, H. Ponnekanti, Y. Yazdi, and x. Li, "Elastography: a quantitative method for imaging the elasticity of biological tissues," Ultrasonic imaging 13: 111–134, 1991;

G. E. Trahey, S. M. Hubbard, and O. T. Von Ramm, "Angle independent blood flow detection by frame-to-frame correlation of B-mode images," Ultrasonics 26: 271–276, 1988;

L. S. Wilson and D. E. Robinson, "Ultrasonic measurement of small displacements and deformations of tissues," Ultrasonic Imaging 4: 71–82, 1982; and S. Yagi and K. Nakayama, "Local displacement analysis of inhomogeneous soft tissue by spatial correlation of rf echo signals," Proceedings 1988 World Federation for Ultrasound in Medicine and Biology, 133, 1988.

This approach is possible because the deformation of biological tissues is a relatively smooth function of position. The performance of this has been evaluated in, for example:

M. Bilgen and M. F. Insana, "Deformation models and correlation analysis in elastography," (referenced above);

"Error analysis in acoustic elastography: I. displacement estimation," J. Acoust. Soc. Am. 101(2): 1139–1146, 1997;

"Error analysis in acoustic elastography: II. strain estimation and SNR analysis," J. Acoust. Soc. Am. 101(2): 1147–1154, 1997; and E. I. Cespedes, M. F. Insana, and J. Ophir, "Theoretical bounds on strain estimation in elastography," IEEE Trans. Ultrason. Ferro Freq. Contr. 42(5): 969–972, 1995.

Due to the physical compression applied to the tissue, a somewhat more realistic approximation to the displacement function can be described as a piece-wise linear function:

$$\Delta(x) = \epsilon_i x + D_i, x \in (x_{i-1}, x_i)$$

where $\epsilon$ is a scaling factor (or strain). Analytical and simulation studies have shown, however, that for $\epsilon > 0.05$, even the improved piece-wise conventional cross-correlation method does not accurately estimate the displacement function. One proposal for overcoming this limitation involves a method known as "global temporal stretching." This technique is described in:

"Reduction of signal decorrelation from mechanical compression of tissues by temporal stretching: Application to elastography," Ultrason. Med. Biol. 23(1): 95–105, 1997; and E. I. Cespedes and J. Ophir, "Reduction of image noise in elastography," Ultrasonic Imaging 15: 89–102, 1993.

This technique requires some a priori knowledge of the applied compression. With this knowledge, one can then globally stretch $r_2$ the same amount as the applied compression. In other words, one geometrically transforms $r_2(x)$ above to obtain a stretched post-compression rf echo function, where the transformation is such that the $x_1$ component of $r_2$ is scaled by the factor $(1-\epsilon)$, where $\epsilon$ is the applied total strain.

Global stretching alleviates the problem caused by cross-correlating strained signals by reducing the amount of the strain between $r_1$ and $r_2$ and thus increasing coherence. In the regions where the local strain variation is large, however, the residual strain after stretching can still remain large. Large residual strain leads in turn to large displacement errors and ultimately to high noise values in strain images. Although efforts have been made to average the estimated strain over multiple compression scans to reduce the noise (see, for example, T. Varghese, J. Ophir, and I. Cespedes, "Noise reduction in elastograms using temporal stretching with multicompression averaging," Ultrasound in Med. Biol. 22(8): 1043–1052, 1996), decorrelation errors are a fundamental problem in strain imaging. This is because of a failure of the forward model for deformation on which image formation algorithms are based. Hence, averaging cannot solve the problem completely.

Two other methods for solving this problem are popular: The first approach is to use a block-matching algorithm to perform a low-resolution displacement estimation after global stretching is applied. This method is described in, for example, P. Chaturvedi, M. F. Insana, and T. J. Hall, "2-D companding for noise reduction in strain imaging," IEEE Trans. Ultrason. Ferroelect. Freq. Contr. 45(1): 179–191, 1998;

"Testing the limitations of 2-D local companding in strain imaging using phantoms," IEEE Trans. Ultrason. Ferroelect. Freq. Contr. 45(4): 179–191, 1998; and M. F. Insana, P. Chaturvedi, T. J. Hall, and M. Bilgen, "3-D companding using linear arrays for improved strain imaging," IEEE Ultrasonics Symposium Proc., 97CH36118: 1435–1438, 1997.

According to this method, after the global stretching, the post-compression scan is warped according to the block matching results. With this processing, the strain between pre- and warped post-compression scans is greatly reduced. Cross-correlation is then applied to perform the final displacement estimation. Results of simulations and experiments have shown this to be a more effective technique than others in the prior art, although the results depend on the boundary conditions and the applied deformation.

One improvement in the warping process can be achieved by applying what is known as a "deformable mesh." This algorithm, and analytical support for it, are described in:

M. F. Insana, L. T. Cook, M. Bilgen, P. Chaturvedi, and Y. Zhu, "Maximum-likelihood approach to strain imaging using ultrasound," J. Acoust. Soc. Am. 107(3), 1421–1434, 2000;

Y. Zhu, P. Chaturvedi, and M. F. Insana, "Strain imaging with a deformable mesh," Ultrasonic imaging 21: 127–146, 1999; and Y. Zhu, M. F. Insana, P. Chaturvedi, T. J. Hall, H. Khant, L. T. Cook, and J. M. Gauch, "Deformable mesh algorithm for strain imaging with complex tissue deformation," IEEE Ultrasonics Symposium Proc. 98CH36102: 1769–1772, 1998.

Yet another known approach is to estimate strain directly by an adaptive local stretching algorithm, in which each segment of the echo signals in the post-compression is "stretched" repeatedly in order to find a best match with a segment in the pre-compression echo signals. The estimated stretching factor is then the estimated strain. A problem with this method is that the comparison segment must be large (2 mm) in order to lower the estimation noise; this can result in distortion in the strain images when the object strain varies significantly in the stretch window. This technique is described in:

S. K. Alam and J. Ophir, "Reduction of signal decorrelation for mechanical compression of tissues by temporal stretching: applications to elastography," (referenced above); and S. K. Alam, J. Ophir, and E. E. Konofagou, "An adaptive strain estimator for elastography," IEEE Trans. Ultrason. Ferroelect. Freq. Contr. 45(2): 461–472, 1998.

The standard block matching algorithm, which can be shown to be a variant of a 2-D cross correlation algorithm, is widely used in digital video compression techniques to estimate the motion vectors of rectangular blocks. See H. Gharavi and M. Mills, "Block-matching motion estimation algorithms: new results," IEEE Trans. Circ. and Syst. 37: 649–651, 1990; and J. R. Jain and A. K. Jain, "Displacement measurement and its application in interframe image coding," IEEE Trans. Commun. 29: 1799–1808, 1981.

A hierarchical block matching algorithm has also been developed in order to decrease the computational load of this method; the algorithm has also been adapted for use in tracking tissue motion. See, for example:

M. Bierling, "Displacement estimation by hierarchical block-matching," Proc. Visual Comm. and Image Proc., SPIE 1001: 942–951, 1988;

A. M. Tekalp, "Digital video processing," Prentice Hall, Upper Saddle River, N.J., 1995; and F. Yeung, S. F. Levinson, and K. J. Parker, "Multilevel and motion model-based ultrasonic speckle tracking algorithms," Ultrasound in Med. and Biol. 24(3): 427–441, In order to detect and track edges in an image, an active contour or "snake" model was proposed by M. Kass, A. Witkin, and D. Terzopoulos in "Snakes: active contour models," International Journal for Computer Vision 1: 321–331, 1988, which later evolved into a well known general-technique known as the "deformable model." The deformable model can be used not only to detect 3-D surfaces and track their deformation from a sequence of images, but it can also be used to synthesize complex shapes. This technique is described in:

W. C. Huang and D. B. Goldgof, "Adaptive-size meshes for rigid and non-rigid shape analysis and synthesis," IEEE Transactions on Pattern Analysis and Machine Intelligence 15(6): 611–616, 1993;

"Point correspondence recovery in non-rigid motion using nonlinear finite element modeling," Proceedings of Asian Conference on Computer Vision: 256–259, 1993;

A. Pentland and B. Horowitz, "Recovery of non-rigid motion and structure," IEEE transactions on pattern analysis and machine intelligence 13(7): 730–742, 1991.

D. Terzopoulos and K. Fleischer, "Deformable models," The visual computer 4: 306–331, 1988; and D. Terzopoulos, A. Witkin, and M. Kass, "Constraints on deformable models: recovering 3D shape and nonrigid motion," Artificial intelligence 36: 91–123, 1988.

Motivated by the ideas behind the deformable model, "deformable mesh" algorithms have been developed to estimate non-rigid motions from 2-D images. See, for example, J. Inagawa and T. Maejima, "Non-rigid motion tracking of image sequences based on smoothness constraints," Systems and Computers in Japan 26(2): 45–53, 1995;

Y. Wang and O. Lee, "Active mesh—a feature seeking and tracking image sequence representation scheme," IEEE Trans. Image Process. 3: 610–624, 1994; and "Use of two-dimensional deformable mesh structures for video coding," IEEE Trans. Circuits and Systems Video Techno. 6: 636–659, 1996.

According to this method, the 2-D data space is partitioned by a mesh, which is composed of contiguous and non-overlapping polygons called "patches." The vertices of the polygons are called "nodes," which are used as control points. By interpolating displacements of the nodes, these control points uniquely determine the displacement function over the meshed region. Adjusting nodal displacements, the deformable mesh algorithm tries to match two images by geometrically transforming one of them according to nodal displacements.

By transmitting displacement information only about the nodal points, the deformable mesh algorithm may also be used to compress image data and minimize data transmission. To do so, however, nodal locations must be chosen such that the interpolated images best resemble the original images in a least-squares sense. An energy function is then derived, which measures the matching error between two image frames (for displacement estimation) and reconstruction error (for image reconstruction of the first frame). By minimizing the energy function, these systems obtain displacement estimates and optimal nodal locations at the same time.

As is described by F. Yeung, S. F. Levinson, D. Fu, and K. J. Parker, in "Feature-adaptive motion tracking of ultrasound image sequences using a deformable mesh," IEEE Trans. Medical Imaging 17(6): 945–956, 1998; in "The use of an adaptive mesh for feature tracking in sonoelasticity," Ultrasonic Imaging 20 (1998, abstract), 61; and in the two papers by Y. Zhu referenced above, the deformable mesh algorithm has also been adapted to ultrasonic tissue displacement estimation. In F. Yeung, et al's implementation, B-scans are used as the input data. The unique feature of this implementation is that the original patches are further divided into sub-patches, based on the band-pass energy and the image interpolation error; it is unclear, however, how the band-pass energy and interpolation errors affect the accuracy of displacement estimation.

Current data acquisition systems reported in the literature for elasticity imaging are cumbersome and in most cases inadequate for clinical imaging. Most of these systems are adapted from laboratory data acquisition systems. They generally use motor-driven compression which can provide smooth displacement, but they fail to provide real-time feedback of the tissue strain. Real-time strain image feedback is essential to determine the quality of the acquired data. B-mode image data shows gross tissue motion, but is inadequate to determine when, for example, elevational motion is too large to allow motion tracking. Descriptions of current data acquisition systems for elasticity imaging are provided in:

S. Y. Emelianov, M. A. Lubinski, A. R. Skovoroda, et al., "Reconstructive ultrasound elasticity imaging for renal transplant diagnosis: Kidney ex vivo results," Ultrasonic Imaging 22: 178–194, 2000;

E. I. Cespedes, C. L. de Korte, A. F. W. van der Steen, "Echo decorrelation from displacement gradients in elasticity and velocity estimation," IEEE Trans Ultrason, Ferroelec, Freq Control 46(4): 791–801, 1999;

B. S. Garra, E. I. Cespedes, J Ophir, et al., "Elastography of breast lesions: Initial clinical results," (referenced above);

"Testing the limits of 2-D companding for strain imaging using phantoms" (referenced above), and;

A. Lorenz, H-J. Sommerfeld, M. Garcia-Schurmann, et al., "A new system for the acquisition of ultrasonic multicompression strain images of the human prostate in vivo," IEEE Trans Ultrason, Ferroelec, Freq Control 46(5): 1147–1154, 1999.

In addition, numerous devices are described in the 2000 IEEE Ultrasonics Symposium Proceedings vol. 00CH37121: 1767–1868.

What is needed is a method and a corresponding system for estimating tissue elasticity using ultrasound that has an improved contrast-to-noise ratio as compared with the prior art, that is able to handle large deformations, and that imposes a computational burden low enough to enable at least substantially real-time imaging of the elasticity of tissue within a 2-D imaging region. This invention provides such a method and system.

SUMMARY OF THE INVENTION

The invention provides an ultrasound imaging method and related system implementation according to which a region of interest (ROI) of a patient's body is repeatedly scanned with an ultrasound transducer. Varying stress is then applied to the ROI. First and second ultrasound echo samples are then acquired at first and second stress levels, respectively, with the second stress level differing from the first and with the first and second echo samples each representing the ROI. A reference sample set is then selected among the first ultrasound echo samples. For each of the first samples in the reference sample set, the system searches within a first search region for a corresponding second sample. For selected ones of the first echo samples not in the reference sample set, the system also searches within a second search region for the corresponding second sample. The second search region is smaller than the first search region, measured in number of samples included in the respective search region. The system then estimates displacement of tissue within the ROI from the difference in estimated positions between the first and second samples and therefrom generates and displays a first representation of a function (such as strain) of the estimated tissue displacement.

In the preferred embodiment of the invention, for each sample in the reference sample set, a displacement vector estimate is calculated that has first and second displacement components that correspond to estimated displacement of the respective sample in a first and a second direction, respectively. For at least selected ones of a plurality of non-reference samples, which are selected from the first sample set, the system assigns, as the second displacement component, the calculated second displacement component of the sample in the reference sample set with which the respective non-reference sample is collocated in the second direction. The first displacement component is then calculated corresponding to estimated displacement in the first direction.

The first search region is preferably two-dimensional, with the second search region being one-dimensional. The first direction preferably extends axially from the transducer and the second direction is preferably a lateral direction that is perpendicular to the first direction.

One advantage of the invention is that it enables real-time imaging of displacement, or a function of displacement such as strain. Accordingly, in a real-time embodiment of the invention, the first representation is generated and updated with a frame rate that is fast enough to allow for coordination by a user of transducer movement with the display of the first representation. The invention allows for a frame rate of at least one frame per second; indeed, a rate of several frames per second is achievable.

The invention also includes a dual-mode processing embodiment. In this embodiment, the first representation is generated with a first quality in a real-time mode. In a post-processing, non-real time mode, however, the first and second ultrasound echo data samples are compared and a post-processed displacement estimate of the tissue within the ROI is calculated, after which a second representation of the post-processed displacement estimate is generated with a second quality that is greater than the first quality.

The search region is preferably adjustable based on different criteria, both spatial and temporal, or both. For example, tissue displacement may be estimated as a displacement vector at each of a plurality of reference depths. For each successive reference depth, a measure of reliability of the estimated displacement vector is then calculated and the search region used to compute a subsequent displacement vector estimate is adjusted based on the reliability of the displacement vector estimate for the corresponding sample located at the previous reference depth.

One method for temporal adjustment according to the invention involves storing the first representation of the function of the estimated tissue displacement for a plurality of image frames and then calculating a frame-to-frame displacement difference value for each of a plurality of corresponding samples. The display of each sample having a displacement difference value greater than a predetermined maximum value is then adjusted accordingly, for example, by temporally smoothing the difference values greater than the predetermined maximum.

As another aspect of the preferred embodiment of the invention, the second search region is dynamically adjusted. In this embodiment, the dimensions $s_{up}$, $s_{down}$, $s_{left}$, and $s_{right}$ of the search region are adjusted for samples in a neighborhood of a reference base sample as a function of the estimated reliability, where $s_{up}$ and $s_{down}$ are numbers of samples above and below the base sample, respectively, in an axial direction, and $s_{left}$ and $s_{right}$ samples on either side of the base sample in a lateral direction. The parameters $s_{up}$ and $s_{down}$ are then preferably set to a predetermined function of ($\epsilon_{max1}$ * $\delta_1$) and $s_{left}$ and $s_{right}$ are set to a predetermined function of ($\epsilon_{max2}$ * $\delta_2$). Here, $\epsilon_{max1}$ and $\epsilon_{max2}$ are maximum possible strains in the axial and lateral directions, respectively; and $\delta_1$, and $\delta_2$ are distances in the axial and lateral directions, respectively, between the base sample and an assumed optimum second sample. The first samples located in a shallowest portion of the region of interest are preferably used as the reference sample set where the shallowest portion has a depth of $D_{ROI}$, measured in the axial direction, and a width $W_{ROI}$, measured in the lateral direction. For current base samples within the shallowest portion, the first search region is then preferably selected to have the dimensions $s_{up}$, $s_{down}$, $s_{left}$, and $s_{right}$, measured in samples. The second search region is then preferably a sample window centered on the second sample displaced from the current base sample by the amount of the previously estimated displacement of the second sample directly above it in the axial direction.

If needed, a smoothed displacement vector is calculated for selected ones of the first samples in the reference sample set. The displacement vector estimate is then compared with the smoothed displacement vector. If the absolute difference between any component of the displacement vector estimate exceeds a corresponding component of the smoothed displacement vector by a predetermined threshold, the system then sets that individual component of the displacement vector estimate equal to the corresponding component of the smoothed displacement vector. The smoothed displacement vector may be calculated using curve fitting, based, for example, in regression, of the components of the a combined set of individual displacement vectors for the first samples in the reference sample set.

DETAILED DESCRIPTION

Figure 1:
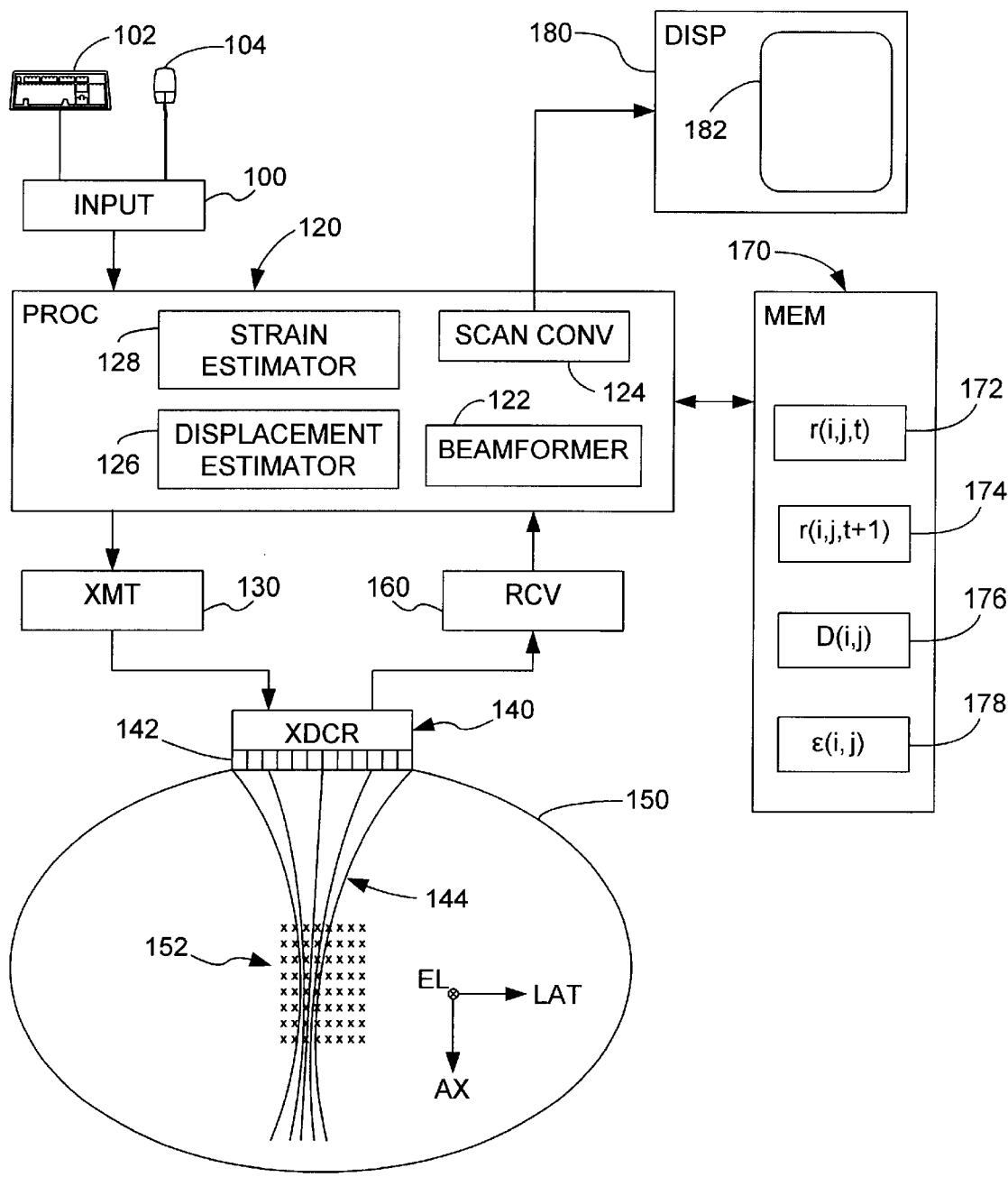
FIG. 1 is a block diagram that illustrates the main components of an ultrasonic imaging system that is suitable for implementing the invention.

The invention provides a method for estimating the strain that arises in a region of a patient's body that is to be imaged using ultrasound and that is subjected to a stress that causes the strain. The source of the strain will usually be the non-constant force of the ultrasound transducer that the user (sonographer or physician) presses against the patient's body during the examination. This makes it possible for the user to easily vary the pressure and see the imaged results. One advantage of the invention is that, even given the processing power now available in ultrasonic imaging systems, it makes it possible to generate a strain image in real time. This means in turn that the user of the invention is able to view a strain display and adjust how he stresses the ROI in order to create an even better strain profile, which then allows the invention to present an even more informative strain display.

Any other conventional device may be used, however, to apply pressure to the surface of the scanned body region and thus to stress the imaged region of interest (ROI); indeed, depending on what portion of the patient's body is to be imaged, the body itself may exert a sufficient time-varying force on the interrogation region. Moreover, the region to be imaged may be pre-stressed, with imaging taking place during tissue relaxation. Note, moreover, that the stress on the ROI may be both positive (causing compression) and negative (causing expansion); the invention is able to estimate strain regardless of the "polarity" of the stress. Before discussing the estimation methods that make this possible, the main hardware components of a system according to the invention are described.

The general method according to the invention is as follows: By pressing an ultrasound transducer against a portion of a patient's body, the tissue within the interrogation region is deformed. Note that, in the context of this invention, deformation will also occur when the user presses the transducer less firmly against the patient: In the normal course of a strain-image scan, the user will apply pressure cyclically because imaging of strain relies on changes in deformation, which lead to displacement (and thus strain) of acoustically reflective structures within the interrogation region.

The interrogation region is also ultrasonically sampled, that is, scanned as in conventional ultrasound imaging, to generate a pattern of ultrasound echo signals representing the acoustically reflective properties within the interrogation region. For at least one pair of consecutive scans, the system according to the invention then calculates an estimate of the displacement function within the interrogation region. Given an estimate of the displacement function, the system then calculates an estimate of the strain distribution function for the samples for which displacement estimates were determined. This estimated strain field is then converted as necessary and displayed in any conventional manner on a system display.

The description below refers frequently to the comparison of a "post-compression" data frame with an earlier generated, "pre-compression" data frame that forms a base or reference frame. This is done simply because it is anticipated that this will be the most common implementation of the invention, but it is not necessary. For example, one could just as well use a later data frame as a reference that is compared with a previously acquired data frame. All that is required for the invention to create a representation of some function of displacement, such as strain, is for the two data frames to be acquired when the ROI is subjected to different levels of stress. (Of course, in the degenerate case, in which the stress level is constant, the invention will still create an accurate, albeit featureless, displacement representation.)

In the description of the invention below, it is assumed that a representation of strain is displayed. Of course, strain is simply a function of displacement; in particular, it is the spatial derivative of the displacement distribution. Especially where the distribution of sample points is uniform in at least one direction, once the system has estimated displacements, it may therefore display any predetermined function of displacement and provide useful information to the user. For example, representations of the displacement estimates themselves could be displayed, scaled or otherwise normalized for the sake of the display.

MAIN SYSTEM COMPONENTS

FIG. 1 illustrates the main components of an ultrasonic imaging system that is suitable for implementing the invention. The user enters various conventional scan parameters into an input unit 100, which typically comprises conventional hardware input ports and any necessary drivers within an operating system and which typically includes such devices as a keyboard 102, knobs, a mouse 104, and/or buttons. The input unit is connected to a processing system 120, which will typically be an electrically connected and cooperating group of processors such as microprocessors and digital signal processors; the processing system may, however, also be implemented by a single processor as long as it is fast enough to handle the various tasks described below.

As in known systems, the processing system 120 sets, adjusts, and monitors the operating parameters of a conventional transmission control circuit 130. This control circuit 130 generates and applies electrical control and driving signals to an ultrasonic probe, that is, transducer 140, which includes an array 142 of piezoelectric elements. As is well known in the art, the piezoelectric elements generate ultrasonic waves when electrical signals of the proper frequency are applied to them.

By placing the probe 140 against the body 150 of a patient, these ultrasonic waves enter a portion (an "interrogation region," or a "region of interest") of the patient's body. By varying the phasing, amplitude, and timing of the driving signals in a conventional manner, the ultrasonic waves from the respective array elements are formed into a transmit beam 144. The beam typically converges at a focal depth, beyond which it once again diverges. The transmit beam is steered in the azimuth/lateral direction LAT and the elevation direction EL, and is focused in the depth/axial direction AX so as to concentrate the ultrasonic energy of the beam onto desired points (indicated as a pattern of "x's" 152) within the interrogation region. In FIG. 1, for example, the beam 144 is shown as being steered just left of the array centerline, that is, the line that would extend from the center of the array and perpendicular to it.

In the description of the invention below, it is assumed that the ultrasound scan produces a 2-D data set, that is, scanning is done in a plane. Without loss of generality, and for ease of illustration, it is assumed that the data set is acquired in the axial-lateral plane, where the axial (AX) dimension corresponds to the return of an acoustic wavefront along a beamline, whereas the lateral direction (LAT) is a spatial dimension, along different beamlines.

Given the description of the invention below, those skilled in the art of designing diagnostic ultrasonic imaging systems will also know how to extend the various 2-D procedures below to 3-D imaging and processing: In essence, instead of processing echo signal information from points on a scan plane, information from samples within a scan volume will be indexed and processed. Instead of 2-D search regions and windows, any 3-D embodiment will use 3-D equivalent search volumes and windows. In addition, although the description below implies a linear array with parallel acoustic beams, those skilled in the art of designing diagnostic ultrasonic imaging systems will also know how to extend this work to other array technologies, such as phased arrays and curved linear arrays.

When any point in the interrogation region is insonified, the transducer is typically switched from the transmit mode to a receive mode. In the receive mode, ultrasonic energy from the waves created by the elements 142 is reflected back (backscattered) as a return echo signal to the array. As is well understood, the piezoelectric elements 142 in the array 140 convert the small mechanical vibrations caused by the echo signal into corresponding radio-frequency (RF) electrical signals. Amplification and other conventional signal conditioning is then applied to the return signals by a reception controller 160. This processing includes, as needed, such known signal conditioning as time-gating, gain compensation, and diffraction compensation, in order to identify the echo signals that correspond to each scanned element in the interrogation region. The type of conventional signal processing needed will in general depend on the particular implementation of the invention and can be chosen using known design methods.

The reception controller 160, all or part of which is normally integrated into the processing system 120 itself, converts the ultrasonic, radio-frequency (RF) return signals (typically on the order of a few to tens of megahertz) into lower frequency ranges for processing, and may also include analog-to-digital conversion circuitry. This is well known in the art of ultrasonic imaging. If not included in the reception controller 160 itself, the processing system 120 will include a beamformer 122 that converts the conditioned return signals into corresponding return beams, each of which normally corresponds to the echo from a transmit beam.

In conventional B-mode scanning, each point within the interrogation region can then be represented as an intensity (brightness) value. The entire interrogation region can therefore be represented as a discretized pattern (matrix) of brightness or signal intensity values, which are stored as frame data in a memory 170.

The interrogation region is normally not in the same shape as what the user wants to see displayed; even when it is, the digital acoustic intensity values that make up the frame data are normally not in a form suitable for driving a conventional gray-tone or color display directly. The acoustic intensity values for a selected 2-D sub-set (scan plane) are therefore applied to a conventional scan converter 124, which converts the digital acoustic values into display intensity values that are suitable for use in driving a display device 180.

The display device 180 typically includes or is connected to a conventional display driver and includes a screen 182 (for example, LED or CRT) that is divided into an X-Y (or polar) matrix or pattern of picture elements or "pixels" that make up an image that the user can view and interpret. Note that a displayed image element will often be made up of more than one pixel, but that this will depend on the relative resolutions of the scan and of the display. The invention does not require any particular relative resolution.

An entire displayable 2-D matrix of intensity values cannot normally be acquired using a single transmit pulse; rather, the brightness for each point in the interrogation region is scanned and converted separately. Nonetheless, scanning is typically fast enough that the brightness values determined for all the points in a given scan plane can be considered to have been acquired at a time t. The next 2-D set of values can be considered to have been acquired at time t+1, where "1" simply indicates the unit of time between completed 2-D scans.

For any given scan plane, the invention stores digital echo signal values for the interrogated point, that is, sample (i,j) in the pattern 152 at both time t and time t+1 for a series of times t; in other words, for each point (i,j), the invention generates and stores the digital echo signal values $r(i,j,t)$ and $r(i,j,t+1)$ for consecutive scans in respective memory portions 172 and 174. As is pointed out below, the digital echo signal values stored are preferably measures of the digital echo signal of the pre- and post-compression radio-frequency (rf) return signals from each of the elements at location (i,j) in the interrogation region. The memory will typically also contain arrays of values that derive from the rf signals, for example, arrays of brightness values used for display. These arrays are not shown in FIG. 1 merely for the sake of simplicity and because they are found in the prior art. The conversion of received signals to brightness values suitable for display is well-understood, and any conventional technique may be used to do so.

One array of values that is not commonly in the prior art, however, is an array 176 that contains displacement estimates $D(i,j)$ for each element (or some predetermined sub-set of elements) in the interrogation region. The displacement values are calculated in a displacement estimation module 126 within the processing system 120. Similarly, the memory also includes an array 178 that contains strain estimates $\epsilon(i,j)$ for each element (or the predetermined sub-set) in the interrogation region. These strain estimates are calculated in a strain estimation module 128 within the processing system 120.

The way in which the displacement and strain values are calculated is explained below. The displacement and strain estimators 126, 128 may be implemented as software components within the larger program controlling the system as a whole, but may also include specialized hardware components such as dedicated digital signal processors if the processing speed and capacity of the existing system processor are not adequate for performing the calculations detailed below fast enough to provide real-time or at least near real time elasticity imaging.

DISPLACEMENT ESTIMATION USING BLOCK MATCHING

Because the estimation of strain within any non-rigid body involves measuring a movement of at least one identifiable point, strain estimation of an interrogation region of a patient's body implies that the region (or some portion of it) is scanned at least twice. One of the difficulties that then arises is that, if the movement is too great, it will be very difficult if not impossible to be certain that a sampled point in the later scan actually corresponds to the same sampled point in the earlier scan. Moreover, sampling and comparing only a small number of points will often cause ambiguity because that set may not be unique in the recorded data.

This limitation can be overcome by matching groups of samples (patches) rather than just individual samples. As long as the waveforms in a patch are unique, such patch-to-patch matching can provide a unique displacement estimate: Because echo waveforms from ultrasound scans are stochastic broad-band signals, the probability of finding an identical set of waveforms in two patches of one image is very small.

In this invention, pre- and post-compression rf echo signals are compared. It is preferable to use the rf return signals because these signals will not yet have been filtered and therefore contain the most "raw" information, which will still contain the phase information (that is, both the I and Q components). Note that this is in contrast to prior art systems, which typically calculate displacement using enveloped echo signals, or rely on feature matching. In both cases, displacement estimates are less precise, since they are based on signals that do not contain phase information, or that have only interpolated estimates for tissue regions between clearly identifiable features.

Figure 2A:
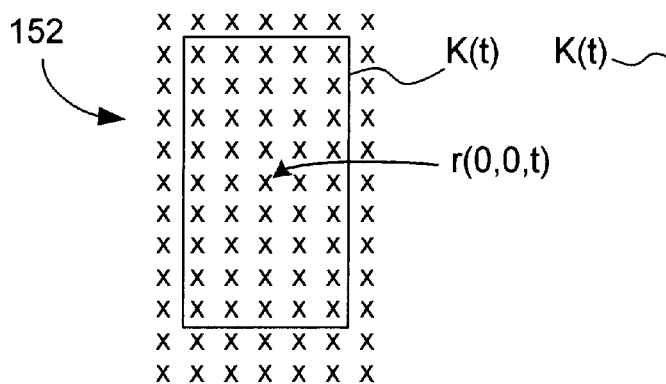
FIG. 2A illustrates a pattern of pre-compression samples in a portion of an interrogation region, as well as a boundary of a kernel used in displacement estimation according to the invention.
Figure 2B:
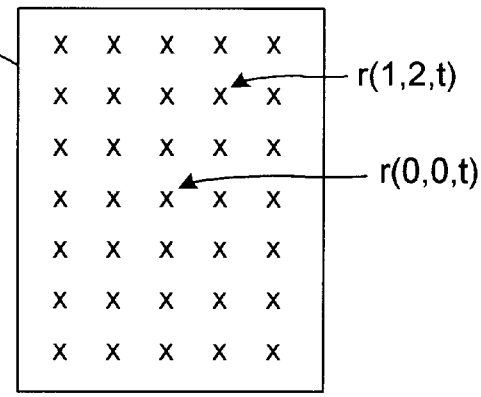
FIG. 2B illustrates the concept of the kernel in greater detail.

See FIG. 2A, in which a scan frame, that is, the pattern 152 of points (shown as "X's") within the interrogation region scanned at pre-compression time t, is represented as rf echo samples $r(i,j,t)$. According to the invention, a "kernel" $K(t)=K(r(i,j,t))$ at time t is then defined as a group of samples located in a window that includes a current node or base sample $r(0,0,t)$. In FIG. 2A, the window, that is, the kernel, is a five-by-nine sample window with the base sample as its center point. This kernel is shown in isolation in FIG. 2B, and two samples $r(0,0,t)$ (the current base sample) and $r(1,2,t)$ are identified.

The size of the kernel may be chosen using normal experimental methods and will depend on such factors as the resolution of the transducer, the scan rate, etc. Increasing the size of the kernel will increase the computational burden of the strain estimation routine, whereas decreasing the size of kernel will in general reduce the reliability of registration between corresponding kernels in consecutive scan frames. Centering the kernel on the base sample is preferred because symmetry will in general provide unbiased information and make indexing easier; other kernels may however, also be used.

As will become clearer below, each sample in the scanned frame (or at least those samples for which strain estimates are to be calculated and displayed) will in turn be used as a base sample. For samples near the edge of the interrogation region, where there are not enough points in one or two directions to allow for a full kernel, either the kernel may be truncated, with corresponding adjustments to the calculations described below, or the samples may simply be deleted from strain estimation calculations altogether—because there will usually be a large number of samples in each direction, ignoring the samples near the edges will normally not cause significant or even noticeable degradation of the display.

Now assume that the interrogation region is subjected to a pressure that causes deformation, that is, movement of acoustically reflective structures within the interrogation region. As is mentioned above, the user herself may generate this pressure by varying the force with which she applies the transducer to the surface of the patient's body. The samples within the (that is, each) kernel $K(t)$ will then be displaced to positions corresponding to samples $K(t+1)$. In other words, each sample $r_2(i,j,t)$ will be located at a position $r_2(i,j,t+1)=r_1(i,j,t)+D_r(i,j,t)$, where $D_r(i,j,t)$ indicates the displacement of sample $r_1(i,j,t)$ in the i and j directions. Thus, $K(t+1)=K(r_1(i,j,t)+D_r(i,j,t))$.

Note that $D_r(i,j,t)$ is unknown, which means that $K(t+1)$ is as yet not determined, even though the positions of all the samples in the frame scanned at time t+1 are known—the problem is at this point how best to "match" a kernel in the frame for time t+1 with the known kernel from the frame scanned at time t.

According to the invention, the "best" match between two kernels is defined as the value of $K(t+1)$ that minimizes a cost or energy function. In the preferred embodiment of the invention, this energy function is the sum-square-difference between $K(t)$ and $K(t+1)$. Thus, the value of $D_r(i,j,t)$ is sought that minimizes the following energy function SSD $(D_r)$:

$$SSD(D_r) = \sum_{i,j} (K(t) - K(t+1))^2$$

Expressed in words, what this minimization amounts to is that the kernel $K(t)$ in the first frame at time t is "moved" axially and laterally until the best match is found, defined as the displacement that minimizes the energy function.

A sum-squared-difference (SSD) energy function provides maximum likelihood estimation for Gaussian distributed optimization problems and corresponds to a so-called $L^2$ metric, which has well-known properties and advantages. It has been proven both analytically and experimentally that the matching error is Gaussian distributed; hence, SSD is the optimum choice. On the other hand, calculating the SSD function is computationally more burdensome than some other common metrics. One such alternative is the sum-absolute-difference (SAD) method, in which no squaring (multiplication) operations are required: In the SAD method, the absolute value of the difference between $K(t)$ and $K(t+1)$ are summed for all (i,j) positions, and the value of $D_r$ that minimizes this sum is found as before. Other metrics may of course be used to determine an optimum $D_r$, that is, the displacement vector that minimizes the chosen energy function.

Yet another alternative energy function is a 2-D correlation Cor(m,n) of the two kernels. In this case, however, the "best" match between $K(t)$ and $K(t+1)$ will be where the "cost," that is, the degree of correlation, is at a maximum rather than a minimum. This correlation function will have the following form:

$$Cor(m, n) = \sum_j \sum_k r_{j,k} \times \bar{\tilde{r}}_{j-m,k-n}$$

where $\bar{\tilde{r}}$ is the complex conjugate of the post-compression rf return waveform.

Note that, regardless of the chosen metric (here, a measure of the "goodness" of the match between kernels), this method implies that the displacement vector $D_r$ can take only values that are linear combinations of the axial and lateral sampling vectors: This block-matching routine assumes that a patch (kernel) of the pre-compression echo samples is geometrically translated without deformation to another location in the post-compression echo samples. The translation vector is estimated as $D_r$. In other words, the 2-D displacement function is approximated as a piecewise constant function. This is equivalent to a zero-th order Taylor series expansion of a 2-D function.

Calculating the minimum value of the energy function involves mathematically searching for the kernel $K(t+1)$ that most closely matches the kernel $K(t)$ in the sense determined by the energy function metric. The most obvious way to do this would be to apply a kernel window to every scanned sample in the frame at time t+1 and see which most closely matches $K(t)$. This would, however, be not only very computationally burdensome and thus slow, but it would also be deliberately ignoring known characteristics of the human tissue and the assumed context of ultrasound scanning. In order to determine sample displacement more efficiently, it is therefore preferable to specify a limited search region over which the energy function is calculated, that is, within which the actual displacement of the current base sample is assumed to lie. According to the invention, the search region is specified by using a predicted displacement and a search range that is based on knowledge of the applied compression and boundary conditions.

Figure 2C:
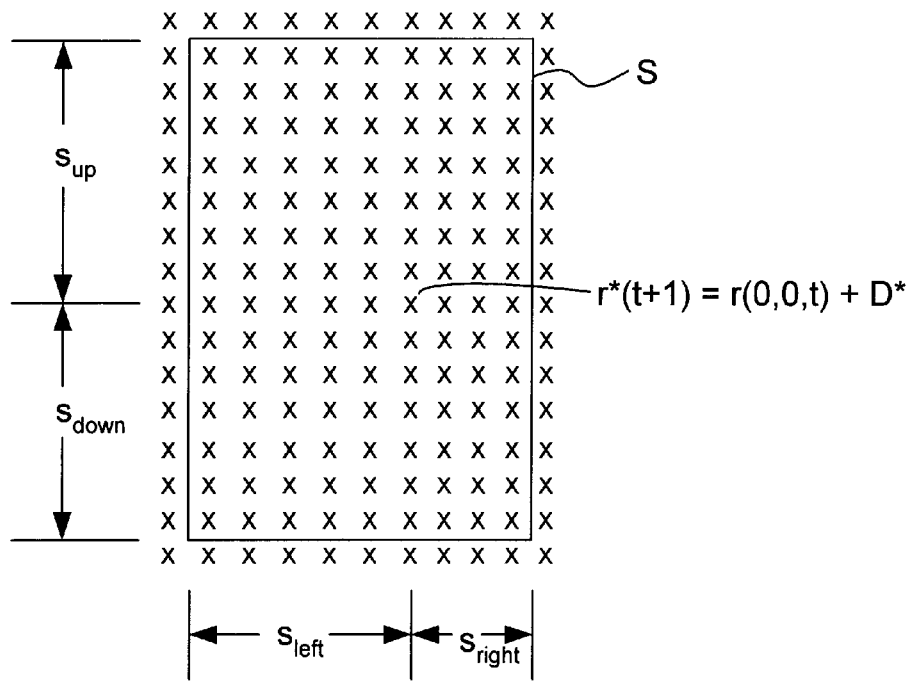
FIG. 2C illustrates a search region in a post-compression echo field used for determining an optimum displacement estimation for a base sample.

FIG. 2C shows a pattern of post-compression return signals (that is, the return signals from corresponding points in the interrogation region). Assume that the pre-compression base sample $r(0,0,t)$ has been displaced to a new position $r*(t+1)=r(0,0,t)+D*$. The position (sample) $r*(t+1)$ is thus a predicted post-compression base sample and $D*$ is a predicted displacement for the pre-compression base sample The actual position of the post-compression base sample (as yet undetermined) is assumed to lie within a search region S that extends from $s_{down}$ samples below to $s_{up}$ sample above, and from $s_{left}$ samples to the left of and $s_{right}$ samples to the right of $r*$. In the illustrated example, $s_{down}$ is not the same as $s_{up}$, and $s_{left}$ is not equal to $s_{right}$. This is simply to illustrate that they need not be equal (for example, at edges of interrogation region. In the preferred embodiment of the invention $s_{down}=s_{up}$ and $s_{left}=s_{right}$, because not only does this simplify indexing for the purpose of computation, but it also accords with the fact that there is no general reason to assume that $r*$ will lie anywhere else but near the center of the search region S.

SEARCH REGION SIZE REDUCTION

To make the block-matching algorithm according to the invention flexible enough to handle any compression-scan configuration, it is wise to assume as little prior knowledge of displacement as necessary. Assuming the predicted displacement is zero everywhere when it is known not to be, however, would require the search region S to become needlessly and sometimes unacceptably large.

Figure 3:
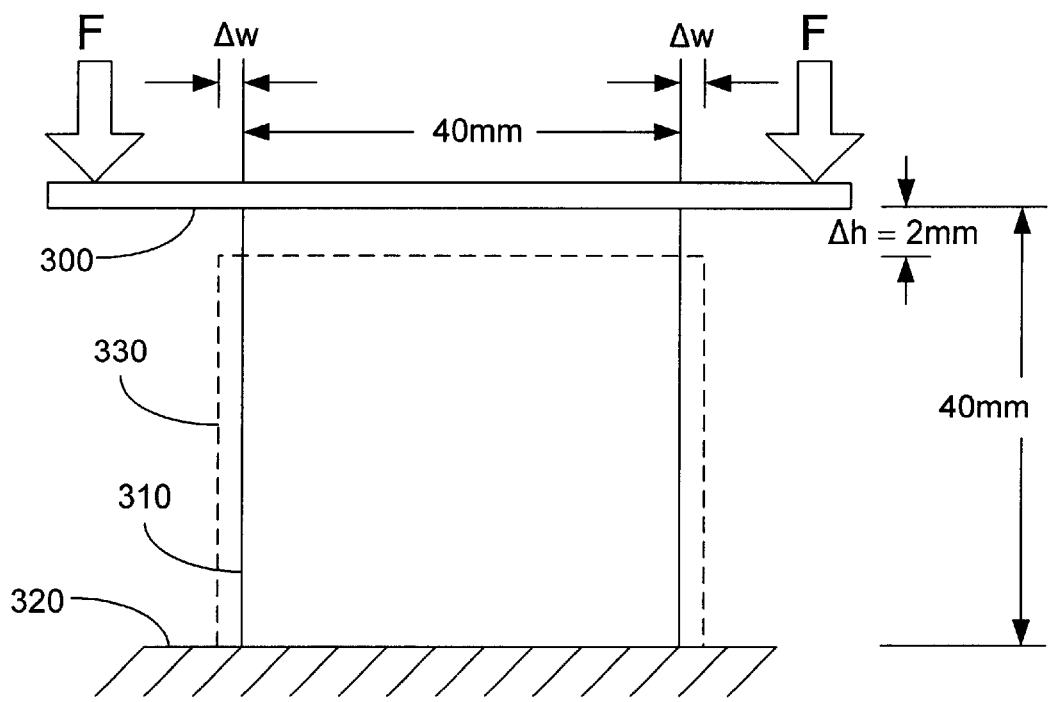
FIG. 3 illustrates the way in which an incompressible block of tissue is deformed under the pressure applied by a user via of an ultrasound transducer plate.

In order to understand how the invention may limit the search region, consider FIG. 3, which illustrates strain in a single plane: Assume that a user presses a flat transducer plate 300 straight down (viewed as in the figure) so that it exerts a force F on a square (here, 40 mm by 40 mm), 2-D scan object 310. This is approximately the size of a typical scan region in ultrasound diagnostic imaging. Assume further that the bottom of the object 310 rests on an immovable base 320, and that the object 310 thereby deforms 5% in the vertical (axial) direction. In this example, the change of height, that is, the vertical displacement, will therefore be $\Delta h=0.05*40$ mm=2 mm.

In ultrasound imaging, it is the transducer that is fixed to the moving compression plate. In echo data, it will therefore appear as if the top of the object is immovable and the bottom of the object 310 is being displaced moving upward. In other words, in the transducer's moving coordinate system, the displacement is 0 mm at top and −2 mm at bottom. Finally, assume that the lateral displacement of the object 310 is zero along the vertical center line; that the contacting surfaces are free to slip at the object boundaries; and that the object is incompressible (Poisson's ratio approximately 0.5). These assumptions are either consistent with or even more restrictive than the conditions found in a normal ultrasound scan.

Under the assumed conditions, the change in width $\Delta h$, that is, the lateral displacement, will be $[(40^2/38)-40]/2=1.05$ mm. For the sake of simplicity, one may round this value to $\Delta h=1.0$.

If the speed of sound is c=1540 m/s, and the temporal sampling frequency of the transducer is 50 MHz, then the axial sampling interval will be $c/(2\times50)=0.0154$ mm. The typical lateral sampling interval of a conventional linear array transducer is roughly 0.2 mm. The bottommost sample will therefore appear to be displaced upward 2/0.0154=130 samples, and the left- and right-most samples are laterally displaced $\pm1/0.2=+5$ samples. This indicates that a search region S (see FIG. 2C) for a base sample located at the bottom of the scanned object would extend about 130 samples below the assumed post-compression base sample and 5 samples on either side; thus, $s_{down}=130$, $s_{up}=0$ and $s_{left}=s_{right}=5$.

In most practical situations where the scanned tissue is elastically heterogeneous, the displacement of a point can be larger than the values assumed in this example. One may therefore enlarge the search region by an experimentally predetermined margin, for example, 10%. Taking all these considerations into account, one may therefore assign $s_{left}=s_{right}=6$; $s_{up}=0$ and $s_{down}=150$ samples (rounded up from 130*1.10=143 for the sake of simplicity). Given these values, there will be a total of $(12+1)*(150+1)=1963$ samples in the search region S. It would therefore be necessary to compute the energy function, for example SSD, 1963 times to determine the most likely displacement D for a given base sample $r(0,0,t)$.

One can generalize this procedure, and in doing so greatly reduce the computational burden. Assume that the search region S has a size of $s_m$ by $s_n$ and that the size of the kernel $K(t)$ is m by n samples. The computational complexity is the number of mathematical operations performed during a task. In this case, the mathematical complexity using the SSD energy function is $s_m*s_n*m*n$ squared-difference computations for block-matching displacement estimation for a single base sample.

The invention provides a method for reducing the computational complexity by reducing the size of the search region without loss of reliability: Let r1 and r2 be two neighboring locations (sample positions) for which displacement is to be estimated. Let $\delta_1$ and $\delta_2$ be assumed axial and lateral distances, respectively, between r1 and r2, which have assumed estimated displacements D1* and D2*. Also assume the maximum possible axial and lateral strains in the object are $\epsilon_{max1}$ and $\epsilon_{max2}$, respectively. The maximum possible axial and lateral displacement differences between the two points will therefore be $\epsilon_{max1}*\delta_1$ and $\epsilon_{max2}*\delta_2$ respectively. Assume now that the estimated displacement D1* for one sample point is a close approximation of the true object displacement. Given the above assumptions, the following is true:

$$|D1^* - D2^*| < \sqrt{(\varepsilon_{max1}\delta_1)^2 + (\varepsilon_{max2}\delta_2)^2} \qquad \text{EQ. 1}$$

In the invention, this expression is used to greatly reduce the size of the search region for any given base sample, for example, r1. According to this method, the system adjusts the size of the search region S to $s_{up}=s_{down}=\text{CEIL}(\epsilon_{max1}*\delta_1)$ and $s_{left}=s_{right}=\text{CEIL}(\epsilon_{max2}*\delta_2)$, where CEIL indicates rounding upward to the nearest larger integer. The parameters $\epsilon_{max1}$, $\epsilon_{max2}$, $\delta_1$, and $\delta_2$ may be determined using normal experimental methods; one example is given below.

To continue the previous example (FIG. 3), assume that the axial and lateral separations of the two nodes r1, r2 are $\delta_1=8$ and $\delta_2=1$ samples, respectively. Let the maximum possible object axial strain $\epsilon_{max1}=0.05$ and lateral strain $\epsilon_{max2}=0.05$, which have been observed in experiments to be sufficiently large strain thresholds in in vivo scanning that, under most conditions, they would lead to decorrelation between pre- and post-compression rf frames. In this case, successful displacement estimation is difficult, if not impossible. In other words, the strain estimation system described in this invention should preferably operate at the compression that generates less than 5% of strain in the consecutive scanning frames. For the new search region, $s_{left}=s_{right}=0.05*1=0.05$ samples and $s_{up}=s_{down}=0.05*8=0.4$ samples. Since search ranges should be limited to be integer numbers of samples, the upward rounded, but still conservative adjusted search region S' will have dimensions $s_{left}=s_{right}=1$ sample and $s_{up}=s_{down}=1$ samples. There are then a total of $(2+1)*(2+1)=9$ samples in the new search region S', which is a reduction by a factor of 218 compared with the original 1963-sample search region S.

According to the invention, the displacement field is estimated on a region of interest (ROI) which is defined in real-time by the user. The ROI is a rectangular sub-region of the scan region. Two or more search regions, S and S', are then preferably used in displacement estimation: A large 2-D search region S is used to estimate displacement for a reference set of samples in the full data field. The size of S is a function of starting depth and width of ROI and the given values of $\epsilon_{max1}$ and $\epsilon_{max2}$. The formulas for determining the size of S in one prototype of the invention were:

$$s_{up}=s_{down}=\text{CEIL}(D_{ROI}*\epsilon_{max1})$$

$$s_{left}=s_{right}=\text{CEIL}(W_{ROI}*\epsilon_{max2})$$

Here, $D_{ROI}$ is the depth of the top of the ROI and $W_{ROI}$ is the width of the ROI; these two parameters define the size of the ROI. CEIL is a rounding function that rounds a number to the nearest larger integer. The size of the ROI is defined by the person who examines the patient. The major criteria a user will apply to select the size of the ROI are the tissue geometry and pathology. $D_{ROI}$ and $W_{ROI}$ may be determined using normal experimental methods and will typically depend on such factors as the type of transducer being used and the type of tissue being imaged. After the displacement of the samples in the reference set is estimated, displacements of the rest of ROI are estimated using search region S' which is defined as:

$$s'_{up}=s'_{down}=s'_{left}=s'_{right}=1$$

The search region S' of a point is thus preferably in a 3-by-3 sample window centered at the sample and displaced from the current base sample by the amount of the previously estimated displacement of the point directly above it, on the same A-line. This guarantees that if the amount of applied compression does not exceeds $\epsilon_{max1}$ and $\epsilon_{max2}$, then the reduced search region will enclose the object displacement at that point. This method implies that the displacement estimation is carried out progressively from a portion of the ROI with the least depth to the portion of the ROI with the largest depth.

Figure 4:
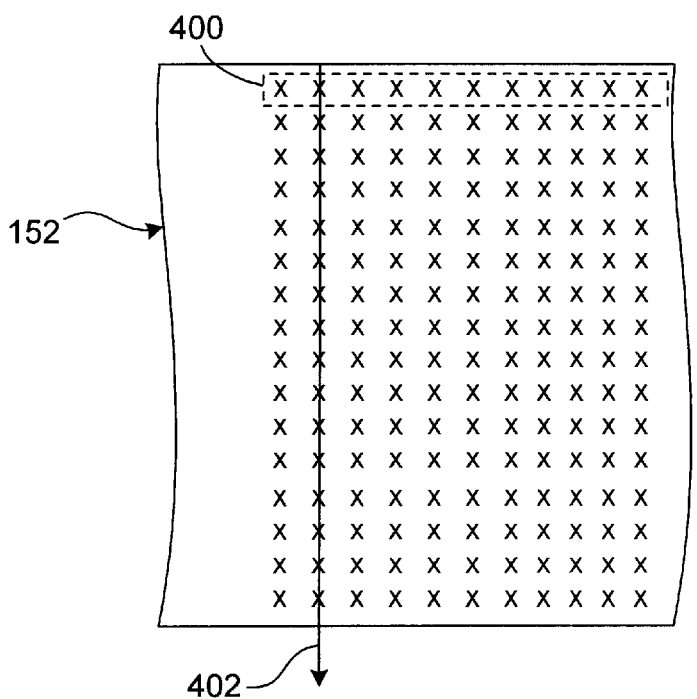
FIG. 4 illustrates the preferred method according to the invention, in which an initial 2-D lateral search is used to track both axial and lateral motion in one or more reference layers and is then followed by a 1-D axial search.

FIG. 4 illustrates the way in which the invention makes use of the general properties of axial and lateral displacement discussed above in order to greatly reduce the computational burden of displacement estimation in order to enable true, real-time imaging of displacement or any function of displacement, such as elasticity. As in the earlier figures, samples within the full data field 152, which makes up the region of interest (ROI), are indicated by "Xs". In FIG. 4, a subset of the samples is indicated within a dotted-line box; these samples form a reference set 400 of samples.

In the preferred embodiment of the invention, a full 2-D search is performed for samples in the reference sample set in order to estimate both axial and lateral displacement for these samples. The value of lateral displacement thus estimated for each sample in the sample set is then assumed to apply to all samples at the same lateral position, that is, on the same A-line. One such A-line 402 is shown in FIG. 4. One result of this assumption is that only axial displacement need be estimated for samples other than those in the reference set; only a 1-D (axial) search is therefore required for these samples.

FIG. 4 shows the preferred choice of reference set, namely, the top row of samples, that is, the row that will lie closest to the transducer. This is preferred because displacement estimates for this row will be the most convenient and easiest to calculate and will generally be the most reliable. It would be possible, however, to chose any other row, for example, one lying near the mid-point in depth of the data field in order to reduce the maximum axial distance over which the reference displacement estimates are propagated.

It is not necessary for the reference set to consist of a single row (same-depth layer) of samples. Rather, 2-D estimation could be applied to all samples in a plurality of adjacent sample rows. The average of the estimated displacement for the reference samples on the same A-line for all the other samples on that A-line. Multi-row 2-D searching would also provide a measure of confidence—if lateral displacement estimates for axially adjacent samples differed by more than a predetermined amount, then the system could either increase the size of the reference sample set until a more consistent value is found, or it could abandon the subsequent 1-D search altogether and signal this to the user.

Recall that typical transducer resolution is much greater in the axial than in the lateral direction. The computational cost of extra reference rows will usually be low enough that the combined 2-D (for reference samples) to 1-D (for all other samples) search procedure according to the invention can still be done in real time.

It would also be possible according to the invention to have multiple reference sample sets. For example, the uppermost row(s) could be used as a primary reference set; the next deepest rows could be used as a secondary reference set, etc. Because it is reasonable to assume that lateral displacement estimates will generally be more reliable for samples closest to the transducer, the size of the 2-D search window and/or kernel could be reduced for the reference samples in the deeper reference sets. The different lateral displacement estimates in the different reference sets can then be checked for consistency or any trends (for example, in the case that the user happens to shear the ROI). Either an average or extrapolated lateral displacement can then be assumed for all non-reference samples on the same A-line. The system could also perform a full 2-D search for a "shallow" reference set, for example, the topmost row, as well as for one or more other non-adjacent sample layers in the ROI (for example, the deepest, or both the deepest and one or more intermediate rows). After checking for consistency (for example, smoothness of change), the system could then apply interpolated lateral displacement values to all other samples on the same A-line as the reference samples.

Two additional mechanisms are preferably included to improve the performance of the method described above. First, there may be errors in the estimated displacement of the top of the ROI and since the search region is large when estimating these displacements, the error can be large. Using the reduced search region directly based on the displacement estimates of the top of the ROI therefore does not always guarantee the correct displacement estimation in the regions where errors occur. Hence, large errors should be removed before the system proceeds to displacement estimation using the reduced search region. The invention provides a procedure that addresses this problem.

Assuming top row (layer) displacement is a smooth function with respect to the lateral locations, then regression may be applied to the top row displacement estimates to generate a curve equation of the form (for the linear case):

$$\delta = ax_1 + b,$$

where i can be 1 or 2 to represent either axial and lateral displacement estimates; $x_1$ is the lateral coordinate of the top row; a and b are estimated coefficients. Each top row displacement estimate is then compared to the value given by the above equation. If the absolute difference between the two values is greater than a threshold, then the displacement estimate is marked as an outlier and its value is replaced by the value obtained from the equation. In other words, regression is used as a smoothing tool. Any large deviation (greater than any experimentally, theoretically or even arbitrarily chosen threshold) from the smoothed value is considered to be a "bad" estimate and replaced by the smoothed value. After this error checking and correcting step, the displacement estimation with the smaller search region S' can be carried out for the rest of the ROI.

There is another problem associated with the reduced search region: In the recorded pre- and post-compression rf frames, it is frequently observed that decorrelation occurs in local regions within the ROI due to the heterogeneous stiffness distribution of the soft tissue. This can cause the incorrect displacement estimation in the local regions. Using small search regions, this mistake may not be recovered when the processing proceeds through the decorrelated local regions. As a result, the mistake caused by decorrelated local regions may propagate throughout the later processing.

To address this issue, the invention preferably includes yet another adjustment procedure, namely, detection and correction of the mistakes caused by local decorrelation using a moving regression method: The displacement estimates are first windowed, then regression is applied within the window to smooth the estimates. Within the window, the displacement estimates are then compared to the smoothed values given by the regression results. For each displacement estimate, if its deviation from the smoothed value exceeds a given threshold, then its value is replaced by the smoothed value. The window is then moved laterally to a new location and the same processing is carried out until every displacement estimate is checked.

Experiments carried out by the inventors have shown that the displacement estimation method introduced above allows the system according to the invention to obtain accurate displacement estimates at a very low computational time for a wide range of actual imaging situations. The general principal for reducing the search region is governed by EQ. 1 above.

It is not necessary to restrict the adjustment of the search region to a two-state choice based on a single threshold determining whether the previously calculated estimate of the displacement vector D is reliable or not reliable, leading to only one small (S') search region and one large (S). Rather, differing degrees of reliability may be implemented, each with a corresponding preferred search region size and associated with a range of goodness values (or other energy/cost values): Along with the estimated displacement for a base sample, the system could also store the goodness value $\eta$ between the base window surrounding it and the window surrounding the sample in the subsequent scan for which the energy function was optimized. When later estimating the displacement of an adjacent sample point, the neighbor's goodness value $\eta$ is examined. The size of the search region for the new (current) sample point is then selected to be the size corresponding to which range of values $\eta$ lies within.

Furthermore, rather than pre-storing a series of search region sizes, the system could calculate some predetermined function of $\eta$ for the neighbor and adjust the dimensions of the current search region accordingly. Let S' be a minimum search region size of $m_{min}$ by $n_{min}$ samples and S be a maximum necessary size (which also includes a margin) with a size of m by n. Moreover, assume that $\eta$ is normalized using any known method to lie in the range $[0, 1]$, where $\eta=1$ implies a perfect match between two kernels. Given the value $\eta$ of the neighboring sample, the search region for a new, current sample point could be set to have the size $m_c$ by $n_c$, where:

$$m_c = \eta * m_{min} + (1-\eta) m_{max}$$

$$n_c = \eta * n_{min} + (1-\eta) n_{max}$$

The greater $\eta$ is, the more the search region is reduced; the maximum search region is used where $\eta=0$.

Of course, other functions may be used to set $m_c$ and $n_c$, for example, those that take into account the fact that the measure of goodness may not vary linearly. A simple linear function such as that shown above will, however, be easier to evaluate.

Furthermore, if goodness values are available for more than one node adjacent to the current node, then some value must be chosen to compare with the threshold(s). One way would be to use the average of the adjacent goodness values. Another method would be to use the lowest adjacent goodness value, which would reduce the chance of choosing a search region that is too small for nodes at structural boundaries where the match may be good in one direction but not in another.

ESTIMATION UNCERTAINTY

Let $e_d$ be a displacement error between the assumed displacement $D^*$ and the actual displacement $D_r$ for the current base sample. Thus, $e_d = D^* - D_r$. According to the invention, displacement precision is determined by calculating the variance $\text{var}(e_d)$ of the estimation error.

The displacement estimates produced by block matching can be considered as a quantization of the object displacement, where the quantization level is the axial sampling interval $\delta_a$. It is known from quantization theory that if the estimation error is uniformly distributed between $-\delta_a/2$ and $+\delta_a/2$, which is a reasonable assumption in the context of ultrasound imaging, then the variance of the estimation error is:

$$\text{var}(e_d) = \delta_a^2/12$$

For a 50 MHz sampling frequency, $\delta_a = 0.0154$ mm so that, theoretically, $\text{var}(e_d) = 1.98 \times 10^{-5}$ mm$^2$. The inventors verified this experimentally by using a prototype of the invention to estimate the displacement of animal tissue at six different levels of total compression, and by then calculating the variance of estimation error. The results were as follows:

TABLE 1

| Compression (%): | 0.5 | 1.0 | 1.5 | 2.0 | 2.5 | 3.0 |
|---|---|---|---|---|---|---|
| var($e_d$)(×10$^{-5}$ mm$^2$): | 2.128 | 2.161 | 2.258 | 2.412 | 2.537 | 2.813 |

These tests therefore showed that, in actual imaging, the variance of the displacement estimation error is close to the theoretical value $1.98 \times 10^{-5}$. The error variance values of the simulated results were, however, slightly higher, but not so far from the theoretical predictions as to merit abandoning the assumption that $\text{var}(e_d) = \delta_a^2/12$.

The relationship $\text{var}(e_d) = \delta_a^2/12$ suggests that the error variance decreases if the sampling interval $\delta_a$ decreases. This suggests in turn that if the sampling interval $\delta_a$ of the rf echo waveform is increased ("up-sampling"), then it would be possible to increase the accuracy of the displacement estimation. The inventors also tested this proposition by up-sampling each scan by a factor of four. The sampling interval $\delta_a$ was therefore reduced to $0.0154/4 = 0.00385$ mm, which gives a predicted error variance $\text{var}(e_d) = 1.24 \times 10^{-6}$. The results, using the same six different compression levels as before, of the estimated displacement with the up-sampled echo field were:

TABLE 2

| Compression (%) | 0.5 | 1.0 | 1.5 | 2.0 | 2.5 | 3.0 |
|---|---|---|---|---|---|---|
| var($e_d$)-(×10$^{-5}$ mm$^2$) | 0.707 | 0.827 | 1.01 | 1.23 | 1.61 | 2.58 |
| $\delta_{\text{eff}}$(mm) | 0.0092 | 0.0100 | 0.0110 | 0.0122 | 0.0139 | 0.0176 |

These values for $\text{var}(e_d)$ are much larger than the predicted value, which demonstrates that the error variance has a lower bound that is independent of the sampling interval. Substituting the values of $\text{var}(e_d)$ listed above into the expression $\text{var}(e_d) = \delta_a^2/12$ gives the sampling intervals at which the lower bounds of error are reached. These computed sampling intervals are "effective" sampling intervals $\delta_{\text{eff}}$. As can be seen above, the effective sampling intervals increase with the amount of applied compression, which suggests that greater compression leads to less precise estimates. This corresponds to theory, because larger compression tends to cause greater decorrelation of pre- and post-compression rf echo waveforms.

Figure 5:
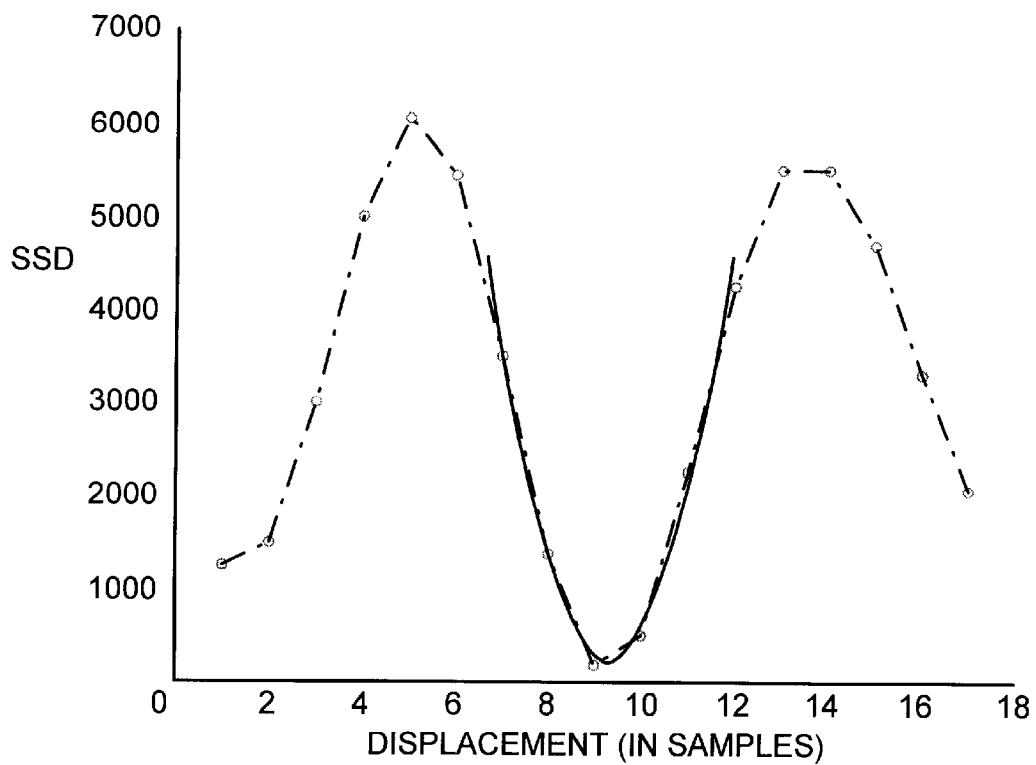
FIG. 5 is a plot of evaluations of a cost or energy function for one test of the invention.

In the preferred embodiment of the invention, for reasons of computational efficiency, the precision of the displacement estimation is increased using a different method, namely, interpolation of the energy function. FIG. 5 illustrates a plot of an actual (test) SSD energy function evaluated as a function of the displacement measured in rf samples (the measured point from which an echo signal has been received, numbered from the shallowest point and deeper in the axial direction). This plot illustrates that the reliability of displacement estimation increases by interpolating the energy function.

From the plot in FIG. 5 it can be seen that several samples of SSD around the minimum closely approximate a quadratic curve. Normal algorithms may be used to generate an approximating quadratic curve for the SSD function in the region of the minimum; one such approximating parabola is shown as a solid curve overlaying the dash-dotted data plot. In the region of the minimum, SSD may therefore be represented as:

$$SSD = a_1 x^2 + a_2 x + a_3$$

which has a minimum for $x = -a_2/(2a_1)$

Since the parameters of the approximating quadratic are known (from whichever standard routine is used to generate the quadratic), this minimum value can be calculated quickly. In the preferred embodiment of the invention, the value of x that gives the minimum for SSD is used as the displacement estimate from the current base sample. Note that even for a large search region the minimum value of SSD will in all practical cases lie no more than about one or two wavelengths away from the true displacement locations. Combined with the fact that all estimates in the first row will already be available, the likelihood that the minimum found is only local is therefore very small. It would of course also be possible to use other optimization routines such as bisection or even simplex, which don't need gradients. Shifting estimated displacements around would then be the same as any other 2-D optimization search.

Using this method of interpolating the measured SSD values for one test scan gave the following results:

TABLE 3

| Compression (%) | 0.5 | 1.0 | 1.5 | 2.0 | 2.5 | 3.0 |
|---|---|---|---|---|---|---|
| var($e_d$)(×10$^{-5}$ mm$^2$) | 0.407 | 0.531 | 0.703 | 0.890 | 1.21 | 1.54 |

It can be seen that the interpolated minimum provides more accurate displacement estimates than up-sampling. Moreover, up-sampling method is computationally more demanding. Determination of the optimum displacement estimate through minimization of an interpolating function of the discrete energy function is therefore the preferred method according to the invention.

One advantage of using a quadratic interpolating function is that it can be generated quickly and has well-understood properties. Other interpolating functions, such as higher order polynomials, or trigonometric functions, etc., may also be used. The type of approximating function used for determining the minimum (or maximum, as the case may be) of the energy function may be chosen using normal design methods, and will also depend on which energy function is employed.

The basic idea of the block matching algorithm according to the invention is that a block of waveforms in the pre-compression rf echo function is matched to another block in the post-compression echo function. Because of compression, however, it would be more accurate to match a block of data from pre-compression to another block of data that is "stretched" (proportional increase in separation) in the axial direction and "squeezed" (proportional decrease in separation) in the lateral direction on the post-compression rf echo function. Such stretching and squeezing are scaling operations, and have the effect of undoing the applied compression geometrically and making the matched blocks have higher coherence. The degree of stretching and squeezing may be predetermined at least approximately by using normal testing techniques, measuring the axial and lateral effects of compression on a test sample of representative tissue.

The inventors investigated the effect of such scaling when using the block-matching method according to the invention. The results showed that stretching the post-compression echo waveform did improve the accuracy in general, but that the improvement in accuracy was too small to justify the computational load associated with the stretching. Stretching may be worthwhile, however, when estimating strain at high levels of compression, for example, at levels above 4% total strain on the scanned interrogation region.

COMPUTATIONAL COMPLEXITY

Assume now that the kernel size for block matching according to the invention is 9×5=45 samples. Except the first row, the search region is reduced to the three-by-three sample size described above. In the worst case, the system will need to compute one additional value of SSD, for a total for a total of 10 SSD evaluations. In the innermost calculation loop, three instructions will be needed on a standard digital signal processor (DSP) to perform two SSD accumulations. In other words, 1.5 instructions are needed for each sample pair. In this example, each displacement estimate will therefore require 45×9×1.5=608 instructions.

Assume now that the size of the region of interest (the interrogation region) is 30 mm by 30 mm. With a 36 MHz axial sampling frequency, the sampling interval is 0.0214 mm. The number of samples for each A-line in the region of interest is therefore 30/0.0214=1402. Now the commonly available lateral sampling interval is 0.2 mm, so that, in the region of interest, there are a total of 150 A-lines.

For reasons of resolution, it will usually not be necessary to calculate a displacement estimate for every sample in a given A-line. Rather, for example, a displacement estimate may be made for every eighth (or some other number, chosen by normal experimental methods) sample axially and every sample laterally, then the total number of displacement estimates is 150×1402/8=26,288.

The total number of instructions needed to compute SSD in this example will therefore be 26,288*608≈1.6×10$^7$. Assume there are 20% more instructions needed to accomplish other computations, such as for first-row displacement estimation, quadratic curve fitting, and strain estimation using linear regression. The total number of instructions needed to generate one strain image will therefore be approximately 1.9×10$^7$. These numbers are estimated based solely on the instructions that are needed for computations. It does not include more time-consuming operations such as internal data transfer, overhead for starting the highly efficient inner loop execution, and image formation and display. On a Sun Spark 10 workstation, the elapsed time needed to process a region of size 30×30 mm$^2$ with a 0.0143 axial sampling interval and a 0.2 mm lateral sampling interval is therefore approximately 2 seconds. Commercially available, specialized DSP chips such as the TMS320C80 of Texas Instruments is capable of executing 2.0×10$^9$ instructions per second. Using such processing technology as the processor within the processing system 120 and the processing method according to the invention, it would therefore be possible to produce at least ten 10 strain images per second, which corresponds to substantially real-time imaging of strain.

REDUCED DIMENSION BLOCK MATCHING

In the description above of the block-matching technique according to the invention, displacement is estimated by searching a 2-D region in order to find a 2-D kernel K(t+1) that best matches the kernel K(t) around the current base sample. It is usually valid to assume, however, that lateral displacement of samples located on a single A-line is relatively uniform. Furthermore, imaging resolution and spatial sampling in depth is usually finer than in the lateral (between A-lines) or elevational directions. These observations can be used to further reduce the computational burden of generating a strain image of the interrogation region, without significantly reducing the quality or contrast of the image in most applications.

In this reduced-dimension embodiment of the invention, a value (or profile) for lateral displacement is first estimated, using the methods described above, for at least one sample on a current A-line. This lateral displacement estimate is then applied to all samples on the same A-line. Alternatively, lateral displacement may be estimated for a sub-set of the samples on the current A-line, for example, every n'th sample (where n is chosen using normal design methods); the assumed lateral displacement for intermediate samples may then be determined by interpolation between the actual estimates. Once lateral displacement has been estimated using the 2-D search described above the system may then switch to a simpler 1-D search in order to estimate axial displacement. The search region S' will in this case be a moving "window" of samples along the same A-line in the vicinity of the current base sample. The advantage of this reduced-dimension technique is that, when lateral displacement has been estimated once (or a relatively few times), it will no longer be necessary to perform 2-D lateral matching calculations at all for the sample on the current A-line. Not only does this reduce the size of the number of summations required in the energy function from two to one, but it also greatly reduces the number of sample pairs for which comparison is needed at all by a full dimension. The reduction in computation time will therefore typically be at least one order of magnitude. This will in turn increase the strain-imaging frame rate for systems with fast processors, and would also make it possible to generate strain images on systems whose processing speed is otherwise not adequate to implement this invention.

TEMPORAL DISPLACEMENT EVALUATION

In the embodiments of the invention described above, a 2-D search is carried out for samples in the reference set(s). The lateral displacement estimates of the reference samples are then assumed to apply to the respective remaining samples on the same A-line; reduced, 1-D searching is then used to determine the axial displacement of these non-reference samples. Various spatial alternatives are also described above for checking and, if needed, improving the reliability of the displacement estimates, especially for the samples in the reference set(s).

It is also possible according to the invention to evaluate a temporal measure of reliability. In this case, a number of frames of displacement data (estimates) may be stored in memory. The frame-by-frame difference in displacement values (corresponding to a sample "acceleration") may then be calculated either for each sample, or as a function (for example, average) of displacement change values for a plurality of samples. For any sample (or sample group) that appears to have a greater than maximum or allowable displacement change, this condition may be either indicated in the ultimate display (for example, by de-emphasizing it by making it colored), or it may be displayed with a temporally (and even spatially) smoothed value until its change value once again comes to within the predetermined acceptable range.

DUAL-MODE PROCESSING

As is described above, the method according to the invention may be performed on either 1-D or 2-D regions of samples: In other words, for each embodiment, the energy functions used to determine the displacement of any given base sample may be optimized with respect to both potential axial and lateral displacements (two-variable optimization, for example, for the reference sample set) or with respect to only potential axial displacement. In the latter case, lateral displacement is either assumed to be negligible, or is for most samples set to be some value determined through calculations for only one or a few samples in the reference set.

As is described above, the computational burden for the reduced-dimension versions of the invention is often at least an order of magnitude less than for the full-scale, 2-D versions. Note, though, that all of the echo signal values necessary for either implementation will always be available—the only issue is how much of the available information is used to calculate the strain distribution of the interrogation region and generate any given strain image. This allows the invention to be operated in either (or both) of two modes: a real-time mode and a post-processing mode.

In the real-time mode, the various mechanisms for reducing computational complexity described above are employed. Although the resolution and accuracy will in most cases be worse, the system may then generate strain image displays at the full frame rate of the conventional B-mode image data on which the displacement estimates are based. The display is then updated fast enough that the user can adjust how he maneuvers the transducer to stress the ROI so as to improve the ability of the system according to the invention to generate accurate displacement and strain estimates. In other words, the update rate of the display is fast enough to allow for feedback to the user's hand-eye coordination system, which in turn allows the user to control modification of the conditions of stressing the ROI. Using the Siemens Elegra ultrasound machine in tests, an update rate of at least five frames per second was achieved using the techniques of the invention; a frame rate of approximately one update per second can therefore easily be achieved, which will in most cases be fast enough to provide information to the diagnostician fast enough to be considered "real time." A frame rate of one frame every two seconds is easily obtainable, although this will often be perceived by the user to be near the approximate limit of "real time" in the sense of being fast enough to enable the user to relate the visual feedback provided by the display to how he maneuvers the transducer. The minimum frame rate necessary to provide a display in this sense of "real time" may be determined experimentally.

As the name implies, in the post-processing mode, immediate display is not required. Rather, all the calculations described above are performed at whatever rate is possible for the given processing system, possibly even beginning after the ultrasound scan is completed. The quality of such a post-processed strain image will in most cases be the highest possible. One way to improve the post-processed quality would be to increase the kernel size for all samples; this would provide a smoother estimated displacement profile, albeit possibly at the cost of reduced resolution. The search region could also be increased, although, as is mentioned above, the maximum necessary search region can in most cases be determined experimentally in advance and will often not need to be very large. Because real-time speed is not required in the post-processing mode, the adaptive search strategy (with reduced-dimensional searching for non-reference samples) is also not required. For example, the system could even up-sample the acquired data (for example, by interpolating the rf signals) before establishing the size of kernels and search regions.

Of course, the system may operate in the real-time mode during the scan and then in the post-processing mode later. In this way, the user may be able to identify features in the lower-quality, real-time strain display that he can then view in greater detail later. Note that several different definitions and measures of "quality" are known and accepted in the art of diagnostic ultrasonic imaging. Any such definition, for example, higher resolution, is applicable to this invention.

In systems that include a "cine mode" which store and allow replay of scan data, the user is usually able to indicate, where the "recording" should stop and start, either by specifying both times, or by making a single entry (for example, pressing a button) that directs the system to store a sequence of frames of a certain number or duration. Using the real-time mode of the invention, the user may see results as she stresses (both positive and negative) the ROI. She can thus "practice" in order to get the feel and see the results of a proper compression/decompression cycle, and then activate cine recording when she sees that the system, in response to her actions, is generating the highest quality strain images. This will in turn provide the best "raw" data for use in later off-line, post-processing of the recorded data; the higher quality post-processing will then be able to generate even better images. This feedback to the user, which is made possible by the real-time capability of the invention, not only saves time, but also increases the reliability of the strain image analysis and reduces the data storage requirements of the system.

STRAIN ESTIMATION

Figure 6:
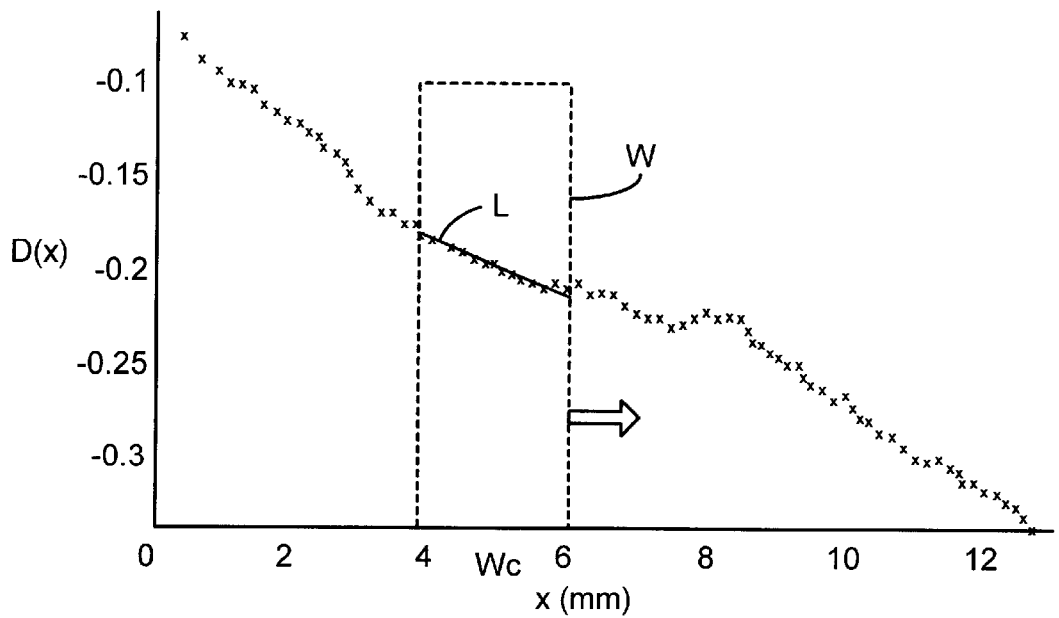
FIG. 6 illustrates a method for strain estimation according to the invention in which linear regression is used within a moving window of displacement estimates.

Once the displacement function has been estimated for the different samples in the interrogation region, it still remains to determine the corresponding strain distribution, since that is the primary property that the invention is designed to estimate and display for the user. FIG. 6 illustrates a typical plot of the estimated displacement D(x), where x is the separation between a chosen base sample and other samples along one A-line in a standard ultrasound phantom with a stiff inclusion located in a region between 4 and 9 mm. By definition, strain is defined as the derivative of the displacement curve, but in actual scans, estimates of displacement the sample values will be noisy.

There are several ways for the system to estimate the displacement derivative from noisy samples. One way is to use a simple difference calculation, that is to calculate, for each A-line sample $r_b$, the value $\epsilon(r_b)$ as:

$$\epsilon(r_1) = (D(r_b) - D(r_j))/\Delta_{sep}$$

Where $D(r_b)$ is the estimated displacement for sample $r_b$, $D(r_j)$ is the estimated strain for the sample located immediately above (or below) $r_b$ in the same A-line, and $\Delta_{sep}$ is the distance between $r_b$ and $r_j$. The same procedure would then be followed for the samples in the adjacent A-line, and so on, until a strain estimate is obtained for all samples in the interrogation region.

Once a strain estimate is calculated (using the difference method or any other method, such as the preferred method described below) for each sample in the interrogation region, any conventional algorithm may be used to scale and convert the estimates into a form suitable for display on the screen 182. One such algorithm is simply to relate each calculated strain value (or range of values) to a corresponding gray-scale value, just as is done in a conventional B-mode ultrasound scan to convert echo intensities into gray-scale display values.

In order to reduce the effect of local anomalies, it would also be possible to calculate $\epsilon(r_1)$ as above for several samples above and/or below the current base sample, and then average (possibly with weighting depending on distance) these strain estimates. This would, however, increase computation time.

It can be shown that it is reasonable to assume that errors in displacement estimations at widely separated locations are uncorrelated. The variance $var(e_\epsilon)$ of the strain estimation error $e_\epsilon$ using the difference method above can be shown to be:

$$var(e_\epsilon) = 2 * var(e_d)/\Delta_{sep}^2$$

The example plot illustrated in FIG. 6 was obtained from a phantom-based test using 2% compression. Assume by way of example that one limits the standard deviation at $e_\epsilon = 0.002$, which is 10% of the total strain, so that $var(e_\epsilon) = 4 \times 10^{-6}$. Using the value $var(e_d) = 8.93 \times 10^{-6}$ from Table 3 above, the separation $\Delta_{sep} = 2.11$ mm.

Using this method and these values in an actual test with three spherical inclusions in a conventional phantom object, the resulting strain image still clearly appeared noisy. In particular, horizontal strain patterns were clearly visible, although no such patterns occurred in the object itself; these horizontal patterns were thus artifacts of the strain estimation method itself.

Another way of estimating the derivative of the displacement curve (an example of which is illustrated in FIG. 6), and thus the strain profile, is to use a "window," that is, the displacement estimates within a portion of the curve, and then to use linear regression to obtain a line that optimally approximates the distribution of the measurements within the window in a least-squares sense. One such window W is illustrated in FIG. 6, with a line segment L shown as the approximating function fitted to the values (shown as "x's") within the window. The value of slope of the line segment L is then determined (for example, from the linear regression algorithm itself) and assigned as the strain estimate for the point $W_c$ located at the center of the window W.

This method of strain estimation by linear regression, within a window that moves (as indicated by the arrow in FIG. 6) over the displacement estimates from samples in the same A-line (same lateral position) was tested with the same test phantom as above, with a window W 2.11 mm wide (the same as $\Delta_{sep}$ in the variance-based method described above). The displayed strain image was noticeably better, with clearly less noise and fewer artifacts.

What is claimed is:

1. An ultrasound imaging method comprising the following steps:

repeatedly scanning a region of interest (ROI) of a body with an ultrasound transducer;

applying varying stress to the ROI;

acquiring first ultrasound echo samples at a first stress level, and second ultrasound echo samples at a second stress level that differs from the first stress level, the first and second echo samples each representing the ROI;

selecting a reference sample set among the first ultrasound echo samples;

for each of the first samples in the reference sample set, searching within a first search region for a corresponding second sample;

for selected ones of the first echo samples not in the reference sample set, searching within a second search region for the corresponding second sample, the second search region being smaller than the first search region, measured in number of samples included in the respective search region;

estimating displacement of tissue within the ROI from the difference in estimated positions between the first and second samples and therefrom generating and displaying a first representation of a function of the estimated tissue displacement.

2. A method as in claim 1, further including the following steps:

for each sample in the reference sample set, calculating a displacement vector estimate having first and second displacement components corresponding to estimated displacement of the respective sample in a first and a second direction, respectively;

for selected samples of the first sample set, which comprise non-reference samples:

for at least selected ones of a plurality of non-reference samples selected from the first sample set:

assigning as the second displacement component the calculated second displacement component of the sample in the reference sample set with which the respective non-reference sample is collocated in the second direction; and calculating the first displacement component corresponding to estimated displacement in the first direction.

3. A method as in claim 2, in which the first search region is two-dimensional and the second search region is one-dimensional.

4. A method as in claim 3, in which the first direction extends axially from the transducer and the second direction is a lateral direction that is perpendicular to the first direction.

5. A method as in claim 2, further including the following steps: for selected ones of the first samples in the reference sample set:

calculating a smoothed displacement vector;

comparing the displacement vector estimate with the smoothed displacement vector; and if the absolute difference between any component of the displacement vector estimate exceeds a corresponding component of the smoothed displacement vector by a predetermined threshold, setting that individual component of the displacement vector estimate equal to the corresponding component of the smoothed displacement vector.

6. A method as in claim 5, in which the smoothed displacement vector is calculated using curve fitting of the components of the a combined set of individual displacement vectors for the first samples in the reference sample set.

7. A method as in claim 6, in which the smoothed displacement vector for each current base sample in the reference sample set is calculated using regression of the components of the displacement vector estimates for the samples within a sample window in the reference sample set.

8. A method as in claim 2, further comprising generating and updating the first representation with a frame rate at least as fast as a predetermined minimum rate necessary for coordination by a user of transducer movement with the display of the first representation.

9. A method as in claim 8, in which the frame rate is at least one frame per second.

10. A method as in claim 2, further including the following steps:
generating the first representation with a first quality in a real-time mode;
in a post-processing, non-real time mode:
comparing the first and second ultrasound echo data samples and
therefrom calculating a post-processed displacement estimate of the tissue within the ROI; and
generating a second representation of the post-processed displacement estimate with a second quality that is greater than the first quality.

11. A method as in claim 2, further including the following steps:
estimating the tissue displacement as an estimated displacement vector at each of a plurality of reference depths; and
for each successive reference depth, calculating a measure of reliability of the estimated displacement vector and adjusting the search region used to compute a subsequent displacement vector estimate based on the reliability of the displacement vector estimate for the corresponding sample located at the previous reference depth.

12. A method as in claim 11, in which the measure of reliability is temporal.

13. A method as in claim 12, further including the following steps:
storing the first representation of the function of the estimated tissue displacement for a plurality of image frames;
calculating a frame-to-frame displacement difference value for each of a plurality of corresponding samples; and
adjusting the display of each sample having a displacement difference value greater than a predetermined maximum value.

14. A method as in claim 13, in which the step of adjusting the display comprises temporally smoothing displacement difference values greater than the predetermined maximum value.

15. A method as in claim 1, in which the predetermined function of the estimated tissue displacement is tissue strain.

16. A method as in claim 1, in which:
A) the steps of acquiring the first and second ultrasound echo samples comprise:
transmitting into the ROI a first and second series of transmit beams of ultrasound, respectively;
for each transmit beam, receiving a corresponding echo signal;
representing the echo signals as the first and second samples, the ROI thereby being represented as at least two-dimensional, first and second arrays of the first and second sample values, respectively;

B) the step of estimating displacement of tissue within the ROI comprises:
i) for at least one current base sample, chosen as one of selected ones of the first samples, selecting a base sample kernel comprising the first sample values located in a current region surrounding the current base sample;
ii) for each of a selection of second samples located in a search region,
a) selecting a second sample kernel having the same dimensions, measured in numbers of samples, as the base sample kernel;
b) calculating an energy function that is a predetermined function of the second sample values within the second sample kernel and corresponding first sample values in the base sample kernel;
iii) designating as an optimum second sample the second sample for which the energy function is optimized;
iv) calculating a displacement vector estimate between the current base sample and the optimum second sample;
C) calculating a display value of a predetermined function of the displacement vector estimate;
D) repeating steps B) and C) for each base sample, thereby generating a corresponding display value for each of the remaining base samples;
E) displaying the display values;
F) estimating the reliability of the displacement vector estimate for at least a reference one of the base samples; and
G) dynamically adjusting the search region as a function of the estimated reliability.

17. A method as defined in claim 1, in which:
the second search region is dynamically adjusted; and
the step of adjusting the search region comprises adjusting dimensions $s_{up}$, $s_{down}$, $s_{left}$, and $s_{right}$ of the search region for samples in a neighborhood of a reference base sample as a function of the estimated reliability, where $s_{up}$ and $s_{down}$ are numbers of samples above and below the base sample, respectively, in an axial direction, and $s_{left}$ and $s_{right}$ samples on either side of the base sample in a lateral direction.

18. A method as in claim 17, further including the steps of setting $s_{up}$ and $s_{down}$ equal to a predetermined function of ($\epsilon_{max1}*\delta_1$) and setting $s_{left}$ and $s_{right}$ equal to a predetermined function of ($\epsilon_{max1}*\delta_2$), where:
$\epsilon_{max1}$ and $\epsilon_{max2}$ are maximum possible strains in the axial and lateral directions, respectively; and
$\delta_1$, and $\delta_2$ are distances in the axial and lateral directions, respectively, between the base sample and an assumed optimum second sample.

19. A method as in claim 18, further comprising:
selecting, as the reference sample set, the first samples located in a shallowest portion of the region of interest, where the shallowest portion has a depth of $D_{ROI}$, measured in the axial direction, and a width $W_{ROI}$, measured in the lateral direction; and
for current base samples within the shallowest portion, selecting the first search region to have the dimensions $s_{up}$, $s_{down}$, $s_{left}$, and $s_{right}$, measured in samples.

20. A method as in claim 19, in which the second search region is a sample window centered on the second sample displaced from the current base sample by the amount of the previously estimated displacement of the second sample directly above it in the axial direction.

21. A method as in 20, in which the second search region comprises a 3-by-3 sample window.

22. An ultrasound imaging method comprising the following steps:
   A) repeatedly scanning a region of interest (ROI) of a body with an ultrasound transducer;
   B) applying varying stress to the ROI;
   C) acquiring first ultrasound echo samples at a first stress level, and second ultrasound echo samples at a second stress level that differs from the first stress level, the first and second echo data samples each representing the ROI;
   D) selecting a reference sample set among first ultrasound echo samples;
   E) for each of the first samples in the reference sample set, which comprise reference samples, searching within a first search region for a corresponding second sample;
   F) for the first samples not in the reference sample set, which comprise non-reference samples, searching within a second search region for the corresponding second sample, the second search region being smaller than the first search region, measured in number of samples included in the respective search region;
   G) for each reference sample, calculating a displacement vector estimate having first and second displacement components corresponding to estimated displacement of the respective reference sample in a first and a second direction, respectively;
   H) for each non-reference sample:
      i) assigning as the second displacement component the calculated second displacement component of the reference sample in the reference sample set with which the respective non-reference sample is collocated in the second direction; and
      ii) calculating the first displacement component corresponding to estimated displacement in the first direction;
   I) estimating displacement of tissue within the ROI from the difference in estimated positions between the first and second samples and therefrom generating and displaying a first representation of a function of the estimated tissue displacement; and
   J) generating and updating the first representation with a frame rate at least as fast as a predetermined minimum rate necessary for coordination by a user of transducer movement with the display of the first representation.

23. An ultrasound imaging method comprising the following steps:
   A) repeatedly scanning a region of interest (ROI) of a body with an ultrasound transducer;
   B) applying varying stress to the ROI;
   C) acquiring first ultrasound echo samples at a first stress level, and second ultrasound echo samples at a second stress level that differs from the first stress level, the first and second echo data samples each representing the ROI;
   D) selecting a reference sample set among first ultrasound echo samples;
   E) for each of the first samples in the reference sample set, which comprise reference samples, searching within a first search region for a corresponding second sample;
   F) for the first samples not in the reference sample set, which comprise non-reference samples, searching within a second search region for the corresponding second sample, the second search region being smaller than the first search region, measured in number of samples included in the respective search region;
   G) estimating displacement of tissue within the ROI from the difference in estimated positions between the first and second samples and therefrom generating and displaying a first representation of a function of the estimated tissue displacement;
   H) for each reference sample, calculating a displacement vector estimate having first and second displacement components corresponding to estimated displacement of the respective reference sample in a first and a second direction, respectively;
   I) for each non-reference sample:
      i) assigning as the second displacement component the calculated second displacement component of the reference sample in the reference sample set with which the respective non-reference sample is collocated in the second direction; and
      ii) calculating the first displacement component corresponding to estimated displacement in the first direction;
   J) generating the first representation with a first quality in a real-time mode;
   K) in a post-processing, non-real time mode:
      i) comparing the first and second ultrasound echo data samples and therefrom calculating a post-processed displacement estimate of the tissue within the ROI; and
      ii) generating a second representation of the post-processed displacement estimate with a second quality that is greater than the first quality.

24. An ultrasound imaging method comprising the following steps:
   A) repeatedly scanning a region of interest (ROI) of a body with an ultrasound transducer;
   B) applying varying stress to the ROI;
   C) acquiring first ultrasound echo samples at a first stress level, and second ultrasound echo samples at a second stress level that differs from the first stress level, the first and second echo data samples each representing the ROI;
   D) selecting a reference sample set among first ultrasound echo samples;
   E) for each of the first samples in the reference sample set, which comprise reference samples, searching within a first search region for a corresponding second sample;
   F) for the first samples not in the reference sample set, which comprise non-reference first samples, searching within a second search region for the corresponding second sample;
   G) estimating displacement of tissue within the ROI from the difference in estimated positions between the first and second samples and therefrom generating and displaying a first representation of a function of the estimated tissue displacement;
   in which:
   H) the second search region is smaller than the first search region, measured in number of samples included in the respective search region;
   I) the steps of acquiring the first and second ultrasound echo samples comprise:
      i) transmitting into the ROI a first and second series of transmit beams of ultrasound, respectively;
      ii) for each transmit beam, receiving a corresponding echo signal;

iii) representing the echo signals as the first and second samples, the ROI thereby being represented as at least two-dimensional, first and second arrays of the first and second sample values, respectively;

J) the step of estimating displacement of tissue within the ROI comprises:
   i) for at least one current base sample, chosen as one of selected ones of the first samples, selecting a base sample kernel comprising the first sample values located in a current region surrounding the current base sample;
   ii) for each second sample located in a search region, which comprises the second samples located within a second sample kernel,
      a) selecting a second sample kernel having the same dimensions, measured in numbers of samples, as the base sample kernel;
      b) calculating an energy function that is a predetermined function of the differences between the second sample values within the second sample kernel and corresponding first sample values in the base sample kernel;

further comprising the following steps:

K) designating as an optimum second sample the second sample for which the energy function is optimized;

L) calculating a displacement vector estimate between the current base sample and the optimum second sample;

M) calculating a display value of a predetermined function of the displacement vector estimate;

N) repeating steps B)-E) for each base sample, thereby generating a corresponding display value for each of the remaining base samples;

O) displaying the display values;

P) estimating the reliability of the displacement vector estimate for at least a reference one of the base samples; and Q) dynamically adjusting the search region a function of the estimated reliability.

25. An ultrasound imaging system comprising:

means for applying varying stress to a region of interest (ROI) of a body;

an ultrasound transducer forming means for repeatedly scanning the ROI and for acquiring first ultrasound echo samples at a first stress level, and second ultrasound echo samples at a second stress level that differs from the first stress level, the first and second echo data samples each representing the ROI;

processing means:
   for selecting a reference sample set among first ultrasound echo samples;
   for each of the first samples in the reference sample set, which comprise reference samples, for searching within a first search region for a corresponding second sample;
   for the first samples not in the reference sample set, which comprise non-reference samples, for searching within a second search region for the corresponding second sample, the second search region being smaller than the first search region, measured in number of samples included in the respective search region; and displacement estimation means, included within the processing means, for estimating displacement of tissue within the ROI from the difference in estimated positions between the first and second samples and therefrom for generating and displaying a first representation of a function of the estimated tissue displacement.

26. A system as in claim 25, in which the displacement estimation means is further provided:

for each reference sample, for calculating a displacement vector estimate having first and second displacement components corresponding to estimated displacement of the respective reference sample in a first and a second direction, respectively;

for each non-reference sample:
   for assigning as the second displacement component the calculated second displacement component of the reference sample in the reference sample set with which the respective non-reference sample is collocated in the second direction; and
   for calculating the first displacement component corresponding to estimated displacement in the first direction.

27. A system as in claim 26, in which the displacement estimation means is further provided:

for generating the first representation with a first quality in a real-time mode;

in a post-processing, non-real time mode:
   for comparing the first and second ultrasound echo data samples and therefrom calculating a post-processed displacement estimate of the tissue within the ROI; and
   for generating a second representation of the post-processed displacement estimate with a second quality that is greater than the first quality.

28. A system as in claim method as in claim 25, further including:

strain estimation means for computing, for converting the estimated tissue displacement into strain values; and display means for displaying the strain values.

* * * * *